US007476516B2

United States Patent
Tang et al.

(10) Patent No.: US 7,476,516 B2
(45) Date of Patent: Jan. 13, 2009

(54) METHODS FOR PRODUCING BIOLOGICAL SUBSTANCES IN PIGMENT-DEFICIENT MUTANTS OF *BACILLUS* CELLS

(75) Inventors: Maria Tang, Fairfield, CA (US); Alan Sloma, Davis, CA (US); David Sternberg, Davis, CA (US); Regine Behr, Roseville, CA (US)

(73) Assignee: Novozymes, Inc., Davis, CA (US)

( * ) Notice: Subject to any disclaimer, the term of this patent is extended or adjusted under 35 U.S.C. 154(b) by 97 days.

(21) Appl. No.: 10/627,124

(22) Filed: Jul. 25, 2003

(65) Prior Publication Data

US 2004/0096944 A1 May 20, 2004

Related U.S. Application Data

(60) Provisional application No. 60/398,853, filed on Jul. 26, 2002.

(51) Int. Cl.
*C12P 21/06* (2006.01)
(52) U.S. Cl. .................... 435/69.1; 435/69.3; 435/69.7; 435/71.1; 435/243; 435/252.1; 435/252.3; 435/252.31
(58) Field of Classification Search ............. 435/69.1, 435/69.3, 69.7, 71.1, 243, 252.1, 252.3, 252.31
See application file for complete search history.

(56) References Cited

OTHER PUBLICATIONS

Bowie et al., Science 247:1306-1310.*
http://www.dsmz.de/microorganisms/bacterial_nomenclature_info.php?bnu_no=0379 2004.*
Kuffer et al., 1967, Archiv für Mikrobiologic 56: 9-21.
MacDonald, 1967, Canadian Journal of Microbiology 13: 17-20.
Uffen and Canale-Parola, 1972, Journal of Bacteriology 111: 86-93.
E. Canale-Parola, 1963, Archiv für Mikrobiologic 46: 414-427.

* cited by examiner

*Primary Examiner*—Jennifer E Graser
(74) *Attorney, Agent, or Firm*—Robert L. Starnes

(57) ABSTRACT

The present invention relates to methods of producing a heterologous biological substance, comprising: (a) cultivating a mutant of a parent *Bacillus* cell under conditions conducive for the production of the heterologous biological substance, wherein (i) the mutant cell comprises a first nucleic acid sequence directing synthesis of the heterologous biological substance and a second nucleic acid sequence comprising a modification of at least one of the genes cypX and yvmC, which are involved in the production of a red pigment, and (ii) the mutant cell is deficient in the production of the red pigment compared to the parent *Bacillus* cell when cultivated under the same conditions; and (b) recovering the heterologous biological substance from the cultivation medium. The present invention also relates to mutants of *Bacillus* cells and methods for producing the mutants.

24 Claims, 14 Drawing Sheets

```
      M  S  Q  S  I  K  L  F  S  V  L  S  D  Q  F  Q  N  N  P  Y  A  Y  F
  1   ATGAGCCAATCGATTAAATTGTTTAGTGTGTGCTTTCTGATCAATTTCAAAACAATCCATATGCTTATTTT

S  Q  L  R  E  E  D  P  V  H  Y  E  E  S  I  D  S  Y  F  I  S  R  Y
 70   TCACAACTGCGGGAGGAAGATCCGGTTCATTATGAAGAGTCGATAGACAGTTATTTTATCAGCCGCTAT

H  D  V  R  Y  I  L  Q  H  P  D  I  F  T  T  K  S  L  V  E  R  A  E
139   CATGATGTCCGCTATATCCTTCAGCATCCGGATATCTTCACGACGAAATCACTTGTTGAGCGTGCCGAA

P  V  M  R  G  P  V  L  A  Q  M  H  G  K  E  H  S  A  K  R  R  I  V
208   CCAGTCATGCGAGGCCCTGTGCTGGCCCAAATGCATGGAAAAGAACACTCTGCCAAAGAAGAATTGTA

V  R  S  F  I  G  D  A  L  D  H  L  S  P  L  I  K  Q  N  A  E  N  L
277   GTGAGAAGCTTTATCGGTGACGCACTGGATCATCTGTCTCCATTAAACAAATGCAGAAAACTTG

L  A  P  Y  L  E  R  G  K  S  D  L  V  N  D  F  G  K  T  F  A  V  C
346   TTAGCGCCTTATCTTGAAAGAGGGAAAAGTGATCTCGTCAATGATTTTGGAAAGACGTTTGCGGTGTGC

V  T  M  D  M  L  G  L  D  K  R  D  H  E  K  I  S  E  W  H  S  G  V
415   GTCACGATGGACATGCTCGGGCTGGATAAAAGAGACCATGAGAAAAATCTCTGAGTGGCACAGCGGAGTT

A  D  F  I  T  S  I  S  Q  S  P  E  A  R  A  H  S  L  W  C  S  E  Q
484   GCCGATTTTATCACGAGTATCTCTCAATCTCCTGAAGCGCGGGCACATTCGTTATGGTGCAGCGAACAG

L  S  Q  Y  L  M  P  V  I  K  E  R  R  V  N  P  G  S  D  L  I  S  I
553   CTTTCCCAATACTTGATGCCGGTCATTAAAGAACGTCGCGTCAATCCGGGATCAGATTTAATTTCGATC
```

Fig. 1A

```
       L  C  T  S  E  Y  E  G  M  A  L  S  D  K  D  I  L  A  L  I  L  N  V
 622   CTATGTACTTCTGAATATGAAGGCATGGCGCTGTCGGACAAGGATATACTCGCACTGATTCTTAATGTG

L  L  A  A  T  E  P  A  D  K  T  L  A  L  M  I  Y  H  L  L  N  N  P
 691   CTGTTAGCCGCAACGGAACCGGCTGATAAGACGCTGGCACTGATGATCTACCATTTGCTCAACAATCCT

E  Q  M  N  D  V  L  A  D  R  S  L  V  P  R  A  I  A  E  T  L  R  Y
 760   GAGCAGATGAATGATGTTTTGGCTGACCGTTCGTTAGTTCCGAGAGCCATTGCGGAGACATTGCGTTAT

K  P  P  V  Q  L  I  P  R  Q  L  S  Q  D  T  V  G  G  M  E  I  K
 829   AAACCGCCGGTTCAGCTGATTCCGCGGCAGCTGTCCCAAGATACAGTGGTCGGCGGTATGGAAATCAAA

K  D  T  I  V  F  C  M  I  G  A  A  N  R  D  P  E  A  F  E  Q  P  D
 898   AAAGATACGATTGTTTTTTGTATGATCGGGGCTAACCGGGACCCTGAAGCATTTGAACAGCCTGAC

V  F  N  I  H  R  E  D  L  G  I  K  S  A  F  S  G  A  A  R  H  L  A
 967   GTGTTTAATATTCATCGGGAAGATCTTGGTATCAAGAGCGCTTTTAGCGGGGCCGCCCGGCATCTCGCT

F  G  S  G  I  H  N  C  V  G  A  A  F  A  K  N  E  I  E  I  V  A  N
1036   TTCGGATCCGGCATTCATAACTGTGTAGGAGCAGCTTTTGCCAAAAACGAAATCGAAATTGTAGCTAAT

I  V  L  D  K  M  R  N  I  R  L  E  E  D  F  C  Y  A  E  S  G  L  Y
1105   ATTGTGCTGGATAAGATGCGGAATATCAGATTAGAGGAAGATTTTGTTATGCTGAGTCCGGTCTGTAT

T  R  G  P  V  S  L  L  V  A  F  D  G  A
1174   ACACGCGGACCTGTTTCACTTCTCGTTGCGTTTGACGGGGCA
```

Fig. 1B

```
      M  Y  T  L  A  H  T  K  S  K  A  V  L  I  L  Y  T  V  C  F  S  A  F
      GTGTACACTTTGGCTCATACAAAATCAAAGGCAGTATTGATCTTATACACTGTTTGCTTCAGTGCATTT

F  A  S  L  S  Q  N  I  Y  S  P  I  L  P  I  K  E  S  F  H  V  S
 70   TTTGCATCTTTAAGCCAGAACATTTATTCACCTATTCTTCCGATCATTAAAGAATCATTCCATGTTTCC

T  A  M  V  N  L  S  V  S  F  M  I  V  T  A  I  M  Q  I  L  G
139   ACAGCTATGGTGAACCTGTCAGTCTCAGTTTTTATGATTGTGACAGCAATAATGCAAATTATATTAGGA

A  I  D  F  K  G  A  R  I  V  L  I  T  G  I  L  A  T  A  A  A  S
208   GCGATCATTGATTTTAAAGGCGCTCGGATCGTCTTGATTACCGGTATTCTGGCAACGGCAGCAGCCAGC

I  G  C  A  V  T  D  F  T  L  F  L  I  F  R  M  I  Q  A  A  G  S
277   ATCGGGCTGTGCGGTGTGACTGACTTTACCTTGTTTCTGATATTCAGAATGATACAGGCAGCCGGTTCC

A  A  L  P  L  I  A  A  T  T  I  G  Q  L  F  T  G  N  E  R  G  S  A
346   GCAGCACTGCCTCTTATTGCTGCCACAACGATCGGACAGCTGTTTACAGGAAATGAACGGGGAGTGCA

M  G  T  Y  Q  M  L  L  S  V  A  P  A  I  A  P  V  L  G  G  F  I  G
415   ATGGGAACGTATCAAATGCTCCTGTCTGTCGCACCGGCTATTGCTCCAGTTCTAGGAGGATTCATAGGC

G  A  A  G  Y  E  G  I  F  W  I  L  A  A  I  S  I  V  L  L  V  T  N
484   GGAGCAGCCGGATACGAAGGGATTTTTTGGATACTTGCGGCCATCTCTATCGTTTTGCTGGTGACAAAC

S  I  T  F  P  K  D  S  P  T  E  S  M  Q  Q  A  K  G  N  V  F  A  H
553   AGCATCACCTTTCCTAAAGATTCTCCAACTGAATCTATGCAGCAAGCCAAAGGCAATGTGTTCGCTCAT
```

Fig. 2A

```
       Y   K   S   I   F   T   N   R   T   G   N   V   I   L   T   L   S   F   V   L   F   F   I
 622   TATAAATCAATATTTACAAATCGAACAGGAACGTCATTTGACTTTAAGTTTTGTTCTCTTTTTCATT

Y   F   A   V   I   V   Y   L   P   I   L   L   T   E   H   Y   H   I   D   V   G   I   A
 691   TATTTTGCAGTAATTGTCTACCTCCCAATATTGCTGACAGAGCATTACCATATAGATGTGGGTATAGCA

G   L   L   Y   L   P   L   A   L   S   T   I   A   G   T   F   L   F   K   R   I   Q   A
 760   GGACTGTTATATTTGCCGCTGAGCACTGATTGCCAGGTACGTTTCTGTTTAAAAGAATACAGGCA

K   I   G   L   H   T   L   F   F   I   G   S   N   V   I   A   C   S   I   L   F   A
 829   AAAATCGGGCTGCACACCTTGTTTATCGGAAGCAATGTGATTGCCGCCTGCAGCATCATTTATTTGCT

V   T   H   S   V   S   L   V   L   M   A   L   T   L   A   L   F   G   I   S   M   G   V
 898   GTTACACATTCCGTTTCTCTCGTTCTCATGGCTCTGACGCTGGCACTGTTTGGCATCTCGATGGGGGTT

I   P   P   L   Y   S   T   M   I   T   N   E   F   F   H   N   R   G   S   A   I   G   M
 967   ATTCCTCCCTTGTACTCTACAATGATTACTAATGAATTTGAGCACAACAGAGGGAGTGCAATCGGAATG

F   N   F   I   R   Y   T   G   M   A   A   G   P   M   V   S   A   Y   L   L   T   M   M
1036   TTTAACTTTATCCGATATACAGGCATGGCAGCAGGTCCGATGGTATCTGCCTACTTGCTCACAATGATG

P   S   A   M   S   F   S   L   L   G   L   G   F   A   A   L   S   F   C   L   L   P   P
1105   CCGTCTGCCATGTCCTTTAGCCTCCTAGGCCTTGGATTTGCCGCCATTGAGCTTTTGCCTTCTTCCGCCA

M   F   S   P   Q   K   R   T   K   Q   K   K   H   M
1174   ATGTTTTCGCCGCAGAAGCGCACGAAACAAAAAGCACCACATG
```

Fig. 2B

```
      M  S  D  L  T  K  Q  M  I  Y  D  I  Y  V  R  L  L  H  L  N  E  Q  K
  1   ATGTCTGATTGACAAAACAGATGATATACGTGAGACTGCTGCACCTTAATGAACAAAAA

A  N  T  S  L  Q  Q  F  F  K  E  A  A  E  E  D  V  A  E  I  P  K  N
 70   GCGAACACTTCACTTCAGCAATTTTTTAAGGAGGCCGCAGAAGAGGATGTAGCTGAAATTCCCAAAAAT

M  T  S  I  H  V  I  D  C  I  G  Q  H  E  P  I  N  N  A  G  I  A  R
139   ATGACAAGCATTCACGTCATTGACTGCATCGGCCAGCATGAACCCATTAATAATGCCGGAATTGCCAGA

K  M  N  L  S  K  A  N  V  T  K  I  S  T  K  L  I  K  E  F  I  N
208   AAAATGAACTTATCGAAAGCGAATGTAACGAAAATCAGCACACAAAAACTGATCAAGGAATTCATTAAC

S  Y  Q  L  T  D  N  K  K  E  V  Y  F  K  L  T  R  K  G  R  R  I  F
277   AGCTATCAGCTGACAGATAACAAAAAAGAAGTTTATTTTAAATTAACCCGTAAAGGCAGACGGATTTTC

D  L  H  E  K  L  H  K  K  K  E  L  A  F  Y  Q  F  L  D  S  F  S  Q
346   GACTTACATGAGAAACTGCATAAAAAAAAGGAGCTGGCTTTTTACCAATTCCTCGATTCATTTTCACAA

E  E  Q  K  A  V  L  K  F  L  E  Q  L  T  S  T  L  E  A  E  Q  T  D
415   GAAGAACAAAAGGCTGTATTGAAGTTTCTAGAGCAGTTGACGTCAACACTTGAAGCAGAACAAACCGAT

G  T  P  D  K  P  V  K
484   GGGACTCCAGACAAACCTGTAAAG
```

Fig. 3

```
       M   N   E   M   T   G   M   V   T   E   R   R   S   V   H   F   I   A   E   A   L   T   E
  1  GTGAATGAGATGACCGGAATGGTAACGGAAGAAGGTCTGTGCATTTTATTGCTGAGGCATTAACAGAA

N   C   R   E   I   F   F   R   R   H   V   L   V   G   I   S   P   F   N   S   R   F
 70  AACTGCAGAGAAATATTTGAACGGCGCAGGCATGTTTTGGTGGGGATCAGCCCATTTAACAGCAGTTT

S   E   D   Y   I   Y   R   L   I   G   W   A   K   A   Q   F   K   S   V   L   L
139  TCAGAGGATTATATTTACAGATTAATTGGATGGGCCAAAGCTCAATTTAAAAGCGTTTCAGTTTTACTT

A   G   H   E   A   A   N   L   L   E   A   L   G   T   P   R   G   K   A   E   R   K   V
208  GCAGGGCATGAGGCGGCTAATCTTCTAGAAGCCGCTTGGAACTCCGAGAGGAAAGGCTGAACGAAAAGTA

R   K   E   V   S   R   N   R   R   F   A   E   R   A   L   V   A   H   G   G   D   P   K
277  AGGAAAGAGGTATCACGAAACAGGAGATTTGCAGAAAGAGCCCTTGTGGCTCATGGCGGGGATCCGAAG

A   I   H   T   F   S   D   F   I   D   N   K   A   Y   Q   L   L   R   Q   E   V   E   H
346  GCGATTCATACATTTTCTGATTTTATAGATAACAAAGCCTACCAGCTGTTGAGACAAGAAGTTGAACAT

A   F   F   E   Q   P   H   F   R   H   A   C   L   D   M   S   R   E   A   I   I   G   R
415  GCATTTTTTGAGCAGCCTCATTTTCGACATGCTTGTTTGGACATGTCTCGTGAAGCGATAATCGGGCGT

A   R   G   V   S   L   M   M   E   E   V   S   E   D   M   L   N   L   A   V   E   Y   V
484  GCGCGGGGCGTCAGTTTGATGATGGAAGAAGTCAGTGAGGATATGCTGAATTTGGCTGTGTGGAATATGTC

I   A   E   L   P   F   F   I   G   A   P   D   I   L   E   V   E   E   T   L   L   A   Y
553  ATAGCTGAGCTGCCGTTTTTTATCGGAGCTCCGGATATATTTAGAGGTGGAAGAGACACTCCTTGCTTAT
```

Fig. 4A

```
      H R P W K L G E K I S N H E F S I C M R P N Q
622 CATCGTCCGTGGAAGCTGGGTGAGAAGATCAGTAACCATGAATTTCTATTGTGTATGCGGCCGAATCAA

G Y L I V Q E M A Q M L S E K R I T S E G
691 GGGTATCTCATTGTACAGGAAATGGCGCAGATGCTTTCTGAGAAACGGATCACATCTGAAGGA
```

METHODS FOR PRODUCING BIOLOGICAL SUBSTANCES IN PIGMENT-DEFICIENT MUTANTS OF *BACILLUS* CELLS

CROSS-REFERENCE TO RELATED APPLICATION

This application claims the benefit of U.S. Provisional Application No. 60/398,853, filed Jul. 26, 2002, which application is incorporated herein by reference.

BACKGROUND OF THE INVENTION

1. Field of the Invention

The present invention relates to methods of producing heterologous biological substances in pigment-deficient *Bacillus* mutant cells, methods of obtaining the pigment-deficient *Bacillus* mutant cells, and the pigment-deficient *Bacillus* mutant cells.

2. Description of the Related Art

The pulcherrimins are reddish pigments resulting from chelation of ferric ions by pulcherriminic acid. The pulcherrimins consist of substituted pyrazine rings with isobutyl groups bound to positions 2 and 5, but differ slightly in other structural details (Kuffer et al., 1967, *Archiv für Mikrobiologic* 56: 9-21).

MacDonald, 1967, *Canadian Journal of Microbiology* 13: 17-20, has described the isolation of pulcherrimin from *Bacillus cereus* and *Bacillus subtilis* and its conversion to the free acid pulcherriminic acid. Uffen and Canale-Parola, 1972, *Journal of Bacteriology* 111: 86-93, describe the synthesis of pulcherriminic acid by *Bacillus subtilis*.

Bacilli are well established as host cell systems for the production of native and recombinant proteins or other biological substances. However, *Bacillus* hosts with the desirable traits of increased protein expression and secretion may not necessarily have the most desirable characteristics for successful fermentation, recovery, and purification of biological substances produced by the cells. These processes may not be optimal because of pigment formation requiring removal during the recovery and purification of a biological substance of interest or the pigment may co-purify with the biological substance.

It is therefore an object of the present invention to provide improved *Bacillus* hosts which combine the capacity for expression of commercial quantities of a biological substance while being deficient in the production of red pigment.

SUMMARY OF THE INVENTION

The present invention relates to methods of producing a heterologous biological substance, comprising:

(a) cultivating a mutant of a parent *Bacillus* cell under conditions suitable for the production of the heterologous biological substance, wherein (i) the mutant cell comprises a first nucleic acid sequence directing synthesis of the heterologous biological substance and a second nucleic acid sequence comprising a modification of at least one of the genes cypX and yvmC, which are involved in the production of a red pigment, and (ii) the mutant cell is deficient in the production of the red pigment compared to the parent *Bacillus* cell when cultivated under the same conditions; and (b) recovering the heterologous biological substance from the cultivation medium.

The present invention also relates to red pigment-deficient *Bacillus* mutant cells and methods for producing the red pigment-deficient *Bacillus* mutant cells.

BRIEF DESCRIPTION OF THE FIGURES

FIGS. 1A and 1B show the genomic DNA sequence of the cypX gene and its deduced amino acid sequence (SEQ ID NOS: 1 and 2, respectively).

FIGS. 2A and 2B show the genomic DNA sequence of the yvmA gene and its deduced amino acid sequence (SEQ ID NOS: 3 and 4, respectively).

FIG. 3 shows the genomic DNA sequence of the yvmB gene and its deduced amino acid sequence (SEQ ID NOS: 5 and 6, respectively).

FIGS. 4A and 4B show the genomic DNA sequence of the yvmC gene and its deduced amino acid sequence (SEQ ID NOS: 7 and 8, respectively).

DETAILED DESCRIPTION OF THE INVENTION

Figure 5:
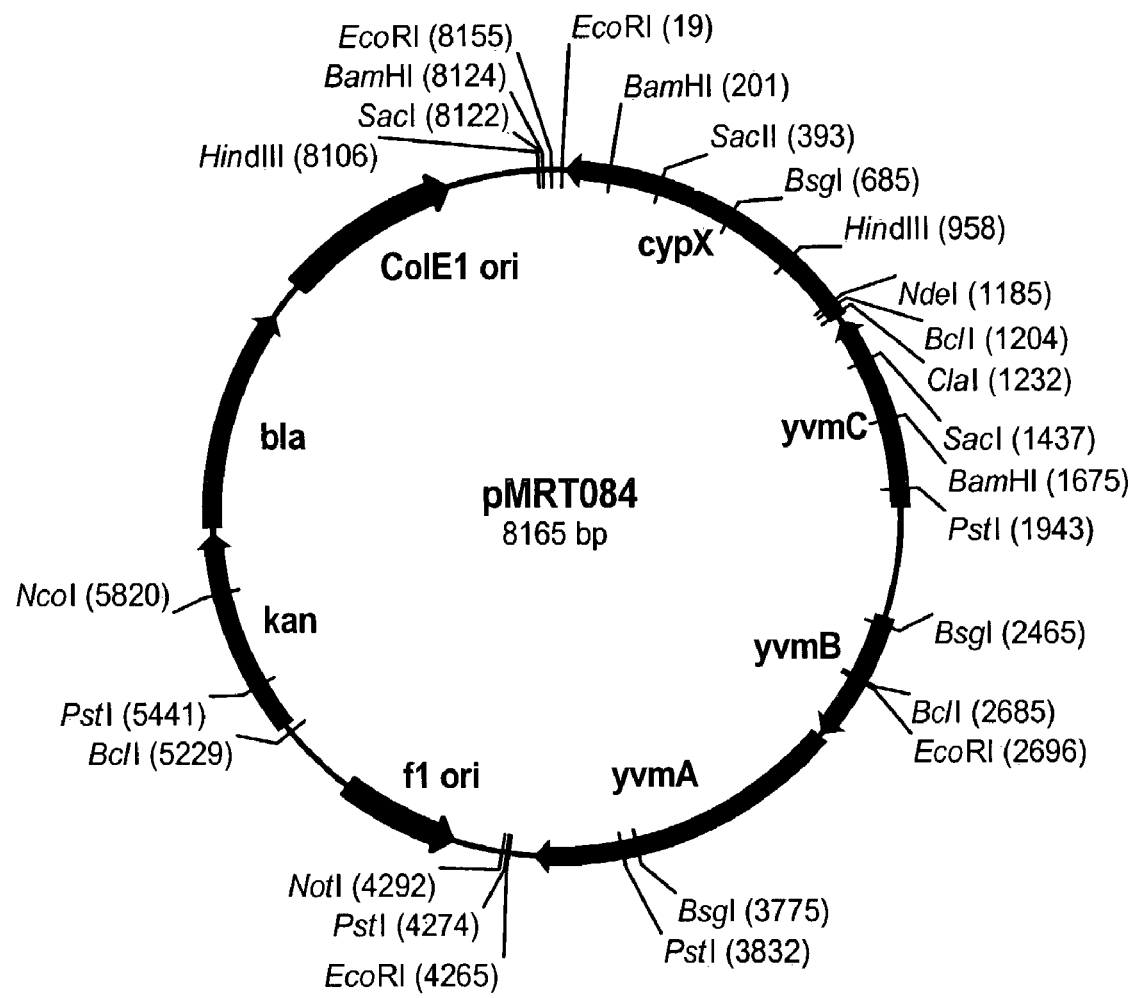
FIG. 5 shows a restriction map of pMRT084.

The present invention relates to methods of producing a heterologous biological substance, comprising: (a) cultivating a mutant of a parent *Bacillus* cell under conditions conducive for the production of the heterologous biological substance, wherein (i) the mutant cell comprises a first nucleic acid sequence directing synthesis of the heterologous biological substance and a second nucleic acid sequence comprising a modification of at least one of the genes cypX and yvmC, which are involved in the production of a red pigment, and (ii) the mutant cell is deficient in the production of the red pigment compared to the parent *Bacillus* cell when cultivated under the same conditions; and (b) recovering the heterologous biological substance from the cultivation medium.

An advantage of the present invention is the elimination or reduction of the red pigment in a *Bacillus* fermentation broth. The elimination or reduction of the red pigment facilitates the recovery and purification of a biological substance of interest.

In the methods of the present invention, the red pigment is believed to be pulcherrimin because when a solid or liquid medium of a *Bacillus* culture is cultivated in the absence of ferric ions and then exposed to ferric ions, the culture and/or cells becomes reddish in color. Moreover, the isolated pigment is soluble in alkali, insoluble in water and organic solvents, and the UV-visible spectrum matches the previously published spectrum for pulcherriminic acid (see, Canale-Parola, 1963, *Archiv für Mikrobiologie* 46: 414-427). The term "pulcherrimin" is defined herein as a ferric chelate or ferric salt of pulcherriminic acid. Pulcherriminic acid is the free acid of pulcherrimin, which consists of substituted pyrazine rings with isobutyl groups bound to positions 2 and 5, which may differ slightly in other structural details (Kuffer et al., 1967, supra).

The term "modification" is defined herein as an introduction, substitution, or removal of one or more nucleotides in the gene or a regulatory element required for the transcription or translation thereof; a gene disruption; gene conversion; a gene deletion; or random or specific mutagenesis of at least one of the genes cypX and yvmC. The deletion of the cypX and/or yvmC gene(s) may be partial or complete.

The phrase "deficient in the production of the red pigment" is defined herein as a *Bacillus* mutant cell which produces no detectable red pigment, or, in the alternative, produces preferably at least about 25% less, more preferably at least about 50% less, even more preferably at least about 75% less, and most preferably at least about 95% less red pigment compared to the parent *Bacillus* cell when cultivated under the same conditions. The level of red pigment produced by a *Bacillus* mutant cell of the present invention may be determined using methods well known in the art (see, for example, Kuffer et al., 1967, supra). However, the presence or absence of the red pigment can be made visually by centrifugation of the cell mass because the pigment adsorbs to the cells, whether the cultivation medium employed is a complex or minimal medium. In a minimal medium, the red pigment can be observed in the supernatant, but as the medium become more complex and colored from the medium components, the color of the components may mask the presence or absence of the red pigment in a cell supernatant.

In the methods of the present invention, the parent *Bacillus* cell may be a wild-type *Bacillus* cell or a mutant thereof, which produces the red pigment. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells. In a preferred embodiment, the *Bacillus* cell is a *Bacillus amyloliquefaciens, Bacillus lentus, Bacillus licheniformis, Bacillus stearothermophilus* or *Bacillus subtilis* cell. In a more preferred embodiment, the parent *Bacillus* cell is a *Bacillus amyloliquefaciens* cell. In another more preferred embodiment, the parent *Bacillus* cell is a *Bacillus clausii* cell. In another more preferred embodiment, the parent *Bacillus* cell is a *Bacillus licheniformis* cell. In another more preferred embodiment, the parent *Bacillus* cell is a *Bacillus subtilis* cell.

The red pigment-deficient mutant cell may be constructed by reducing or eliminating expression of at least one of the genes cypX and yvmC using methods well known in the art, for example, insertions, disruptions, replacements, or deletions. The portion of the gene to be modified or inactivated may be, for example, the coding region or a regulatory element required for expression of the coding region. An example of such a regulatory or control sequence may be a promoter sequence or, a functional part thereof, i.e., a part which is sufficient for affecting expression of the nucleic acid sequence. Other control sequences for possible modification include, but are not limited to, a leader, propeptide sequence, signal sequence, transcription terminator, and transcriptional activator.

The *Bacillus* mutant cells may be constructed by gene deletion techniques to eliminate or reduce the expression of at least one of the genes cypX and yvmC. Gene deletion techniques enable the partial or complete removal of the gene(s) thereby eliminating their expression. In such methods, the deletion of the gene(s) may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, for example, Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C.).

The *Bacillus* mutant cells may also be constructed by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, Science 229: 4719; Lo et al., 1985, *Proceedings of the National Academy of Sciences USA* 81: 2285; Higuchi et al., 1988, *Nucleic Acids Research* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The *Bacillus* mutant cells may also be constructed by gene disruption techniques by inserting into one or more of the genes responsible for the production of the red pigment an integrative plasmid containing a nucleic acid fragment homologous to the gene(s) which will create a duplication of the region of homology and incorporate vector DNA between the duplicated regions. Such gene disruption can eliminate gene expression if the inserted vector separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The *Bacillus* mutant cells may also be constructed by the process of gene conversion (see, for example, Iglesias and Trautner, 1983, *Molecular General Genetics* 189: 73-76). For example, in the gene conversion method, a nucleic acid sequence corresponding to the gene(s) is mutagenized in vitro to produce a defective nucleic acid sequence which is then transformed into the parent *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (see, for example, Pereago, 1993, supra). Alternatively, the defective nucleic acid sequence may contain an insertion, substitution, or deletion of one or more nucleotides of the gene, as described below.

The *Bacillus* mutant cells may also be constructed by established anti-sense techniques using a nucleotide sequence complementary to the nucleic acid sequence of the gene (Parish and Stoker, 1997, *FEMS Microbiology Letters* 154: 151-157). More specifically, expression of the gene by a *Bacillus* cell may be reduced or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The *Bacillus* mutant cells may be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp 363-433, Academic Press, New York, 1970) and transposition (see, for example, Youngman et al., 1983, *Proc. Natl. Acad. Sci. USA* 80: 2305-2309). Modification of the gene may be performed by subjecting the parent cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent cell to be mutagenized in the presence of the mutagenizing agent of choice under suitable conditions, and selecting for mutant cells exhibiting reduced or no expression of the gene.

In the methods of the present invention, either the cypX or yvmC gene, or both, of a *Bacillus* cell involved in the production of the red pigment may be modified, as described herein. The cypX-yvmC operon was identified as a potential site involved in the formation of the red pigment by *Bacillus* ORFs microarray analysis according to the protocol of Berka et al., 2002, *Molecular Microbiology* 43: 1331-1345. It will be understood that the term "second nucleic acid sequence" may include one or both of the genes-cypX and yvmC.

In a preferred embodiment, cypX comprises a nucleic acid sequence having at least 70%, preferably at least 75%, more preferably at least 80%, even more preferably at least 85%, most preferably at least 90%, and even most preferably at least 95% homology to SEQ ID NO: 1. In a most preferred embodiment, cypX comprises the nucleic acid sequence of SEQ ID NO: 1. In another most preferred embodiment, cypX consists of the nucleic acid sequence of SEQ ID NO: 1.

In a preferred embodiment, yvmC comprises a nucleic acid sequence having at least 70%, preferably at least 75%, more preferably at least 80%, even more preferably at least 85%, most preferably at least 90%, and even most preferably at least 95% homology to SEQ ID NO: 7. In a most preferred embodiment, yvmC comprises the nucleic acid sequence of SEQ ID NO: 7. In another most preferred embodiment, yvmC consists of the nucleic acid sequence of SEQ ID NO: 7.

For purposes of the present invention, the degree of homology between two nucleic acid sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

A nucleic acid sequence homologous or complementary to the nucleic acid sequences described herein, involved in the production of the red pigment, may be used from other microbial sources which produce the red pigment to modify the corresponding gene in the *Bacillus* strain of choice.

In a preferred embodiment, the modification of a gene involved in the production of a red pigment in the *Bacillus* mutant cell is unmarked with a selectable marker.

Removal of the selectable marker gene may be obtained by culturing the mutants on a counter-selection medium. Where the selectable marker gene contains repeats flanking its 5' and 3' ends, the repeats will facilitate the looping out of the selectable marker gene by homologous recombination when the mutant cell is submitted to counter-selection. The selectable marker gene may also be removed by homologous recombination by introducing into the mutant cell a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

It will be understood that the methods of the present invention are not limited to a particular order for obtaining the *Bacillus* mutant cell. The modification of the gene(s) involved in the production of the red pigment may be introduced into the parent cell at any step in the construction of the cell for the production of a biological substance. It is preferable that the *Bacillus* mutant cell has already been made red pigment-deficient prior to the introduction of a gene(s) directing synthesis of a heterologous biological substance.

In a further aspect of the present invention, the mutants of *Bacillus* cells may additionally contain modifications, e.g., deletions or disruptions, of other genes which may be detrimental to the production, recovery or application of a biological substance. In a preferred embodiment, the *Bacillus* cell is a protease-deficient cell. In a more preferred embodiment, the *Bacillus* cell comprises a disruption or deletion of aprE and nprE. In another preferred embodiment, the *Bacillus* cell does not produce spores. In another more preferred embodiment, the *Bacillus* cell comprises a disruption or deletion of spoIIAC. In another preferred embodiment, the *Bacillus* cell comprises a disruption or deletion of one of the genes involved in the biosynthesis of surfactin, e.g., srfA, srfB, srfC, and srfD. See, for example, U.S. Pat. No. 5,958,728. Other genes, e.g., the amyE gene, which are detrimental to the production, recovery or application of a biological substance may also be disrupted or deleted.

In the methods of the present invention, the *Bacillus* mutant cell preferably produces at least the same amount of the biological substance as the corresponding parent *Bacillus* cell when cultured under identical production conditions. In a more preferred embodiment, the mutant cell produces at least about 25% more, preferably at least about 50% more, more preferably at least about 75% more, and most preferably at least about 100% more of the biological substance than the corresponding parent *Bacillus* cell when cultured under identical production conditions.

The *Bacillus* mutant cells are cultivated in a nutrient medium suitable for production of the heterologous biological substance using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted biological substance can be recovered directly from the medium.

The biological substances may be detected using methods known in the art that are specific for the biological substances. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

The resulting biological substance may be isolated by methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989). A metabolite of interest may be isolated from a cultivation medium by, for example, extraction, precipitation, or differential solubility, or any method known in the art. The isolated metabolite may then be further purified using methods suitable for metabolites.

The heterologous biological substance may be any biopolymer or metabolite. The biological substance may be encoded by a single gene or a series of genes composing a biosynthetic or metabolic pathway. Thus, the term "first nucleic acid sequence directing synthesis of a heterologous biological substance" will be understood to encompass one or more genes involved in the production of the biological substance. The term "heterologous biological substance" is defined herein as a biological substance which is not native to the host cell; a native biological substance in which structural modifications have been made to alter the native biological substance, e.g., the protein sequence of a native polypeptide; or a native biological substance whose expression is quantitatively altered as a result of a manipulation of the host cell by recombinant DNA techniques, e.g., a stronger promoter.

In the methods of the present invention, the biopolymer may be any biopolymer. The term "biopolymer" is defined herein as a chain (or polymer) of identical, similar, or dissimilar subunits (monomers). The biopolymer may be, but is not limited to, a nucleic acid, polyamine, polyol, polypeptide (or polyamide), or polysaccharide.

In a preferred embodiment, the biopolymer is a polypeptide. The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include hybrid polypeptides, which comprise a combination of partial or complete polypeptide sequences obtained from at least two different polypeptides wherein one or more may be heterologous to the *Bacillus* cell. Polypeptides further include naturally occurring allelic and engineered variations of the above-mentioned polypeptides and hybrid polypeptides.

Preferably, the heterologous polypeptide is an antibody, antigen, antimicrobial peptide, enzyme, growth factor, hormone, immunodilator, neurotransmitter, receptor, reporter protein, structural protein, and transcription factor.

In a preferred embodiment, the heterologous polypeptide is an oxidoreductase, transferase, hydrolase, lyase, isomerase, or ligase. In a more preferred embodiment, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In a preferred embodiment, the biopolymer is a polysaccharide. The polysaccharide may be any polysaccharide, including, but not limited to, a mucopolysaccharide (e.g., heparin and hyaluronic acid) and nitrogen-containing polysaccharide (e.g., chitin). In a more preferred embodiment, the polysaccharide is hyaluronic acid.

In the methods of the present invention, the metabolite may be any metabolite. The metabolite may be encoded by one or more genes. The term "metabolite" encompasses both primary and secondary metabolites. Primary metabolites are products of primary or general metabolism of a cell, which are concerned with energy metabolism, growth, and structure. Secondary metabolites are products of secondary metabolism (see, for example, R. B. Herbert, *The Biosynthesis of Secondary Metabolites*, Chapman and Hall, New York, 1981).

The primary metabolite may be, but is not limited to, an amino acid, fatty acid, nucleoside, nucleotide, sugar, triglyceride, or vitamin.

The secondary metabolite may be, but is not limited to, an alkaloid, coumarin, flavonoid, polyketide, quinine, steroid, or terpene. In a preferred embodiment, the secondary metabolite is an antibiotic, antifeedant, attractant, bacteriocide, fungicide, hormone, insecticide, or rodenticide.

In the methods of the present invention, the mutant of the *Bacillus* cell is a recombinant cell, comprising a nucleic acid sequence directing synthesis of a heterologous biological substance, e.g., polypeptide, which is advantageously used in the recombinant production of the biological substance. The cell is preferably transformed with a vector comprising the nucleic acid sequence directing synthesis of the heterologous biological substance followed by integration of the vector into the chromosome. "Transformation" means introducing a vector comprising the nucleic acid sequence into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the chromosome occurs by homologous recombination, non-homologous recombination, or transposition.

The nucleic acid sequence directing synthesis of a heterologous biological substance may be obtained from any prokaryotic, eukaryotic, or other source, e.g., archaeabacteria. For purposes of the present invention, the term "obtained from" as used herein in connection with a given source shall mean that the biological substance is produced by the source or by a cell in which a gene from the source has been inserted.

In the methods of the present invention, the mutants of *Bacillus* cells may also be used for the recombinant production of biological substances which are native to the *Bacillus* cell.

The native biological substance may be recombinantly produced by, for example, placing a gene(s) directing synthesis of the biological substance under the control of a different promoter to enhance expression of the substance, expediting its export outside the cell by use of, for example, a signal sequence, or increasing the copy number of a gene directing synthesis of the biological substance normally produced by the *Bacillus* cell. Thus, the present invention also encompasses, within the scope of the term "heterologous biological substances," such recombinant production of native biological substances, to the extent that such expression involves the use of genetic elements not native to the *Bacillus* cell, or use of native elements which have been manipulated to function in a manner that do not normally occur in the host cell.

The techniques used to isolate or clone a nucleic acid sequence directing synthesis of a biological substance are known in the art and include isolation from genomic DNA, preparation from cDNA, or a combination thereof. The cloning of the nucleic acid sequences from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence directing synthesis of the biological substance, insertion of the fragment into a vector molecule, and incorporation of the recombinant vector into a *Bacillus* cell where multiple copies or clones of the nucleic acid sequence will be replicated. The nucleic acid sequence may be of genomic, cDNA, RNA, semisynthetic, synthetic origin, or any combinations thereof.

In the methods of the present invention, where the biological substance is a heterologous polypeptide, such a polypeptide may also include a fused polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence. The term "coding sequence" is defined herein as a sequence which is transcribed into mRNA and translated into a biological substance of interest when placed under the control of the below mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence directing synthesis of a biological substance may be manipulated in a variety of ways to provide for expression of the biological substance. Manipulation of the nucleic acid sequence prior to its insertion into a vector may be desirable or necessary depending on the expression vector or Bacillus host cell. The techniques for modifying nucleic acid sequences utilizing cloning methods are well known in the art.

A nucleic acid construct comprising a nucleic acid sequence directing synthesis of a biological substance may be operably linked to one or more control sequences capable of directing the expression of the coding sequence in a mutant of a *Bacillus* cell under conditions compatible with the control sequences.

The term "control sequences" is defined herein to include all components which are necessary or advantageous for expression of the coding sequence of a nucleic acid sequence. Each control sequence may be native or foreign to the nucleic acid sequence directing synthesis of the biological substance. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence directing synthesis of a biological substance.

The control sequence may be an appropriate promoter sequence, a nucleic acid sequence which is recognized by a *Bacillus* cell for expression of the nucleic acid sequence. The promoter sequence contains transcription control sequences which mediate the expression of the biological substance. The promoter may be any nucleic acid sequence which shows transcriptional activity in the *Bacillus* cell of choice and may be obtained from genes directing synthesis of extracellular or intracellular biological substances either homologous or heterologous to the *Bacillus* cell. Examples of suitable promoters for directing the transcription of the nucleic acid constructs of the present invention, especially in a *Bacillus* cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727-3731), as well as the tac promoter (DeBoer et al., 1983, *Proceedings of the National Academy of Sciences USA* 80:21-25). Further promoters are described in "Useful proteins from recombinant bacteria" in *Scientific American*, 1980, 242:74-94; and in J. Sambrook, E. F. Fritsch, and T. Maniatis, 1989, *Molecular Cloning, A Laboratory Manual*, 2d edition, Cold Spring Harbor, N.Y.).

The control sequence may also be a suitable transcription terminator sequence, a sequence recognized by a *Bacillus* cell to terminate transcription. The terminator sequence is operably linked to the 3' terminus of the nucleic acid sequence directing synthesis of the biological substance. Any terminator which is functional in the *Bacillus* cell of choice may be used in the present invention.

The control sequence may also be a suitable leader sequence, a nontranslated region of a mRNA which is important for translation by the *Bacillus* cell. The leader sequence is operably linked to the 5' terminus of the nucleic acid sequence directing synthesis of the biological substance. Any leader sequence which is functional in the *Bacillus* cell of choice may be used in the present invention.

The control sequence may also be a signal peptide coding region, which codes for an amino acid sequence linked to the amino terminus of a polypeptide which can direct the expressed polypeptide into the cell's secretory pathway. The signal peptide coding region may be native to the polypeptide or may be obtained from foreign sources. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a *Bacillus* species. However, any signal peptide coding region capable of directing the expressed polypeptide into the secretory pathway of a *Bacillus* cell of choice may be used in the present invention.

An effective signal peptide coding region for *Bacillus* cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57: 109-137.

In the methods of the present invention, a recombinant expression vector comprising a nucleic acid sequence, a promoter, and transcriptional and translational stop signals may be used for the recombinant production of a polypeptide or other biological substance. The various nucleic acid and control sequences described above may be joined together to produce a recombinant expression vector which may include one or more convenient restriction sites to allow for insertion or substitution of the nucleic acid sequence directing synthesis of the polypeptide or biological substance at such sites. Alternatively, the nucleic acid sequence may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleic acid sequence. The choice of the vector will typically depend on the compatibility of the vector with the *Bacillus* cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the *Bacillus* cell, is integrated into the genome and replicated together with the chromosome(s) into which it has been integrated. The vector system may be a single vector or plasmid or two or more vectors or plasmids which together contain the total DNA to be introduced into the genome of the *Bacillus* cell, or a transposon.

The vectors may be integrated into the *Bacillus* cell genome when introduced into a *Bacillus* cell. For integration, the vector may rely on the nucleic acid sequence directing synthesis of the biological substance or any other element of the vector for stable integration of the vector into the genome by homologous recombination. Alternatively, the vector may contain additional nucleic acid sequences for directing integration by homologous recombination into the genome of the *Bacillus* cell. The additional nucleic acid sequences enable the vector to be integrated into the *Bacillus* cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the *Bacillus* cell. Furthermore, the integrational elements may be non-encoding or encoding nucleic acid sequences.

For autonomous replication, the vector may further comprise an origin of replication enabling the vector to replicate autonomously in the *Bacillus* cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in the *Bacillus* cell (see, e.g., Ehrlich, 1978, *Proceedings of the National Academy of Sciences USA* 75:1433).

More than one copy of a nucleic acid sequence directing synthesis of a biological substance of interest may be introduced into the *Bacillus* cell to amplify expression of the nucleic acid sequence. Stable amplification of the nucleic acid sequence can be obtained by integrating at least one additional copy of the sequence into the *Bacillus* cell genome using methods well known in the art and selecting for transformants. A convenient method for achieving amplification of genomic DNA sequences is described in WO 94/14968.

The vectors preferably contain one or more selectable markers which permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, erythromycin, chloramphenicol or tetracycline resistance. Furthermore, selection may be accomplished by co-transformation, e.g., as described in WO 91/09129, where the selectable marker is on a separate vector.

The procedures used to ligate the elements described above to construct the recombinant expression vectors are well known to one skilled in the art (see, e.g., Sambrook et al., 1989, supra).

The transformation of the *Bacillus* cell may, for instance, be effected by protoplast transformation (see, e.g., Chang and Cohen, 1979, *Molecular General Genetics* 168: 111-115), by using competent cells (see, e.g., Young and Spizize, 1961, Journal of Bacteriology 81: 823-829, or Dubnau and Davidoff-Abelson, 1971, Journal of Molecular Biology 56: 209-221), by electroporation (see, e.g., Shigekawa and Dower, 1988, Biotechniques 6: 742-751), or by conjugation (see, e.g., Koehler and Thorne, 1987, Journal of Bacteriology 169: 5271-5278).

The present invention also relates to methods of obtaining a mutant of a parent Bacillus cell, comprising: (a) introducing into the Bacillus cell a first nucleic acid sequence comprising a modification of at least one of the genes cypX and yvmC, which are involved in the production of a red pigment; and (b) identifying the mutant cell from step (a) comprising the modified nucleic acid sequence, wherein the mutant cell is deficient in the production of the red pigment.

The present invention further relates to mutants of a parent Bacillus cell, comprising a first nucleic acid sequence directing synthesis of a heterologous biological substance and a second nucleic acid sequence comprising a modification of at least one of the genes cypX and yvmC, which are involved in the production of a red pigment, wherein the mutant cell produces less of the red pigment than the parent Bacillus cell when cultivated under the same conditions.

The present invention is further described by the following examples which should not be construed as limiting the scope of the invention.

EXAMPLES

All primers and oligos were supplied by MWG Biotech, Inc., High Point, N.C.

Bacillus subtilis strains were made competent using the method described by Anagnostopoulos and Spizizen, 1961, Journal of Bacteriology 81: 741-746.

DNA sequencing was conducted with an ABI 3700 Sequencing (Applied Biosystems, Inc., Foster City, Calif.).

Example 1

Identification of the cypX-yvmC and yvmB-yvmA operons using DNA Microarrays

Bacillus subtilis strain RB128 is a Bacillus subtilis A164Δ5 strain (Bacillus subtilis ATCC 6051A deleted at the spoIIAC, aprE, nprE, amyE, and srfC genes) obtained according to the methods of U.S. Pat. No. 5,891,701. Bacillus subtilis strain RB128 contains a heterologous gene encoding a Bacillus maltogenic amylase. Bacillus subtilis strain BRG1 was obtained by N-methyl-N'-nitrosoguanidine (NTG) mutagenesis of Bacillus subtilis RB128 according to the following protocol. Bacillus subtilis RB128 cells grown to log phase were treated with three concentrations of N-methyl-N'-nitrosoguanidine (NTG): 0.26 mg/ml, 0.53 mg/ml, and 1.06 mg/ml yielding percent kills of 98.2%, 99.5%, and 99.9%, respectively. One hundred microliters of each treatment was outgrown 6 times in 1 ml aliquots in 24 well plates. The outgrowths were preserved in 10% glycerol and frozen at −80° C. The library size was approximately 15500, 4200, and 250 mutants for each treatment, respectively. The Bacillus subtilis BRG1 mutant was isolated from the 0.26 mg/ml NTG treatment Bacillus subtilis strains RB128 and BRG1 were cultivated for 48 hours at 40-41° C., pH 7±0.2 in 1.5 liters of medium composed per liter of 50 g of hydrolyzed protein, 6.5 g of $KH_2PO_4$, 4.5 of $Na_2HPO_4$, 3.0 g of $(NH_4)_2SO_4$, 2.0 g of $Na_3$-citrate-$2H_2O$, 3.0 g of $MgSO_4$, 0.15 mg of biotin, 0.5 g of $CaCl_2$—$2H_2O$, and trace metals. The fermentations were fed at a maximum rate of 8 g of saccharide per liter per hour. The cultures were sparged with air at 1 to 2 liters per minute and agitated at 1300 rpm. The whole broth color of Bacillus subtilis strain BRG1 was light brown compared to the whole broth of Bacillus subtilis strain RB128 which was dark brown. Red pigment was visible in the cellular pellet of the whole broth from Bacillus subtilis strain RB128, while no red pigment was observed in the Bacillus subtilis strain BRG1 cellular pellet.

Total cellular RNA was obtained from 6, 12, 24, 29 and 46 hour samples (10 ml) of the fermentations of Bacillus subtilis strains RB128 and BRG1. The RNA was obtained from cell pellets prepared from the fermentation samples stored at −80° C. For RNA preparation, the frozen cell pellet was resuspended in 1 ml of diethylpyrocarbonate (DEPC)-treated water, and nine replicates were prepared using the Fast RNA Blue kit (Bio101, Inc., Vista, Calif.). The replicates were then pooled into one tube for preparation of cDNA probes.

Ten replicate cDNA targets per time point were prepared and hybridized to Bacillus subtilis ORFs PCR fragment microarrays according to Berka et al., 2002, Molecular Microbiology 43: 1331-1345 and Kane et al., 2000, Nucleic Acids Research 28: 4552-4557. Bacillus subtilis strain RB128 cDNA was labeled with Cy5 (Amersham Corporation, Arlington Heights, Ill.) while Bacillus subtilis strain BRG1 cDNA was labeled with Cy3 (Amersham Corporation, Arlington Heights, Ill.) according to the procedure of Eisen and Burn, 1999, Methods in Enzymology 303: 179-205. Cy3 (a green fluorescent dye) and Cy5 (red fluorescent dye) reporters were detected with solid state lasers operating at 532 nm and 632 nm, respectively. The arrays were scanned and formatted for analysis with QuantArray (PerkinElmer Lifesciences, Inc., Boston, Mass.) and imported into GeneSpring (Silicon Genetics, Inc., Redwood City, Calif.) for final analysis. Statistical significance analysis of the replicate slides was analyzed with the SAM Excel add-in from Stanford University (Tusher et al., 2001, Proceedings of the National Academy of Sciences USA 98: 5116-5121). The cypX-yvmC and yvmB-yvmA operons were identified as potential sites involved in the formation of the red pigment, pulcherrimin (cypX: FIG. 1, SEQ ID NOs: 1 and 2, accession number BG12580; yvmC: FIG. 2, SEQ ID NOs: 3 and 4, accession number BG14121; yvmB: FIG. 3, SEQ ID NOs: 5 and 6, accession number BG11018; and yvmA: FIG. 4, SEQ ID NOs: 7 and 8, accession number BG14120). The cypX-yvmC and yvmB-yvmA operons were consistently down-regulated in Bacillus subtilis strain BRG1 for the 12-46 hour time-points compared to Bacillus subtilis strain RB128.

A second microarray experiment was performed using two replicate cDNA targets hybridized to Bacillus subtilis ORFs oligonucleotides microarrays. The oligonucleotides were purchased from Compugen, Inc., Jamesburg, N.J. and printed on poly-L-lysine coated slides at a concentration of 10 μM to a density of four Bacillus subtilis genomes per slide as described by Berka et al., 2002, supra. Bacillus subtilis strains RB128 and BRG1 cDNAs were labeled as described above. The arrays were scanned and formatted for analysis using a GenePix 4000B scanner and GenePix Pro version 4.1 software (Axon Instruments, Inc., Union City, Calif.). Statistical significance analysis of the replicate genomes was analyzed with the SAM Excel add-in as above and significant genes identified were imported to GeneSpring version 4.2. In this second microarray experiment, only the cypX-yvmC operon was identified as potential site involved in the formation of the red pigment.

Example 2

Construction of *Bacillus subtilis* strain MaTa17

The cypX-yvmC and yvmB-yvmA operons were PCR amplified from *Bacillus subtilis* strain BRG1 as a single fragment using primers 1 and 2.

```
Primer 1: 5'-CATGGGAGAGACCTTTGG-3'  (SEQ ID NO: 9)

Primer 2: 5'-GTCGGTCTTCCATTTGC-3'   (SEQ ID NO: 10)
```

The amplification reactions (50 µl) were composed of 200 ng of *Bacillus subtilis* BRG1 chromosomal DNA, 0.4 µM each of primers 1 and 2, 200 µM each of dATP, dCTP, dGTP, and dTTP, 1× Expand™ High Fidelity buffer with 1.5 mM $MgCl_2$, and 2.6 units of Expand™ High Fidelity PCR System enzyme mix (Roche Diagnostic Corporation, Indianapolis, Ind.). *Bacillus subtilis* BRG1 chromosomal DNA was obtained using a QIAGEN tip-20 column (QIAGEN, Inc., Valencia, Calif.) according to the manufacturer's instructions (*Genomic DNA Handbook*, QIAGEN, Inc., Valencia, Calif., 1999-2001, pp. 38-47). Amplification reactions were performed in a RoboCycler 40 thermacycler (Stratagene, Inc, La Jolla, Calif.) programmed for 1 cycle at 95° C. for 3 minutes; 10 cycles each at 95° C. for 1 minute, 58° C. for 1 minute, and 68° C. for 4 minutes; 20 cycles each at 95° C. for 1 minute, 58° C. for 1 minute, 68° C. for 4 minutes plus 20 seconds per cycle, followed by 1 cycle at 72° C. for 7 minutes. Reaction products were analyzed by agarose gel electrophoresis using a 0.8% agarose-25 mM Tris base-25 mM borate-0.5 mM disodium EDTA buffer (0.5× TBE) gel.

The resulting fragment comprising the cypX-yvmC and yvmB-yvmA operons was cloned into pCR2.1 using the TA-TOPO Cloning Kit and transformed into *E. coli* OneShot™ cells according to the manufacturer's instructions (Invitrogen, Inc., Carlsbad, Calif.). Transformants were selected on Yeast-Tryptone (2× YT) agar plates supplemented with 100 µg of ampicillin per ml. Plasmid DNA from several transformants was isolated using QIAGEN tip-20 columns according to the manufacturer's instructions and verified by DNA sequencing with M13 (-20) forward, M13 reverse and primers 3 to 18 shown below. M13 (-20) forward and M13 reverse primers were obtained from Invitrogen, Inc, Carlsbad, Calif. The resulting plasmid was designated pMRT084 (FIG. 5).

```
Primer 3:
5'-CGACCACTGTATCTTGG-3'       (SEQ ID NO: 11)

Primer 4:
5'-GAGATGCCAAACAGTGC-3'       (SEQ ID NO: 12)

Primer 5:
5'-CATGTCCATCGTGACG-3'        (SEQ ID NO: 13)

Primer 6:
5'-CAGGAGCATTTGATACG-3'       (SEQ ID NO: 14)

Primer 7:
5'-CCTTCAGATGTGATCC-3'        (SEQ ID NO: 15)

Primer 8:
5'-GTGTTGACGTCAACTGC-3'       (SEQ ID NO: 16)

Primer 9:
5'-GTTCAGCCTTTCCTCTCG-3'      (SEQ ID NO: 17)

Primer 10:
5'-GCTACCTTCTTTCTTAGG-3'      (SEQ ID NO: 18)

Primer 11:
5'-CGTCAATATGATCTGTGC-3'      (SEQ ID NO: 19)

Primer 12:
5'-GGAAAGAAGGTCTGTGC-3'       (SEQ ID NO: 20)

Primer 13:
5'-CAGCTATCAGCTGACAG-3'       (SEQ ID NO: 21)

Primer 14:
5'-GCTCAGCTATGACATATTCC-3'    (SEQ ID NO: 22)

Primer 15:
5'-GATCGTCTTGATTACCG-3'       (SEQ ID NO: 23)

Primer 16:
5'-AGCTTTATCGGTGACG-3'        (SEQ ID NO: 24)

Primer 17:
5'-TGAGCACGATTGCAGG-3'        (SEQ ID NO: 25)

Primer 18:
5'-CATTGCGGAGACATTGC-3'       (SEQ ID NO: 26)
```

Figure 6:
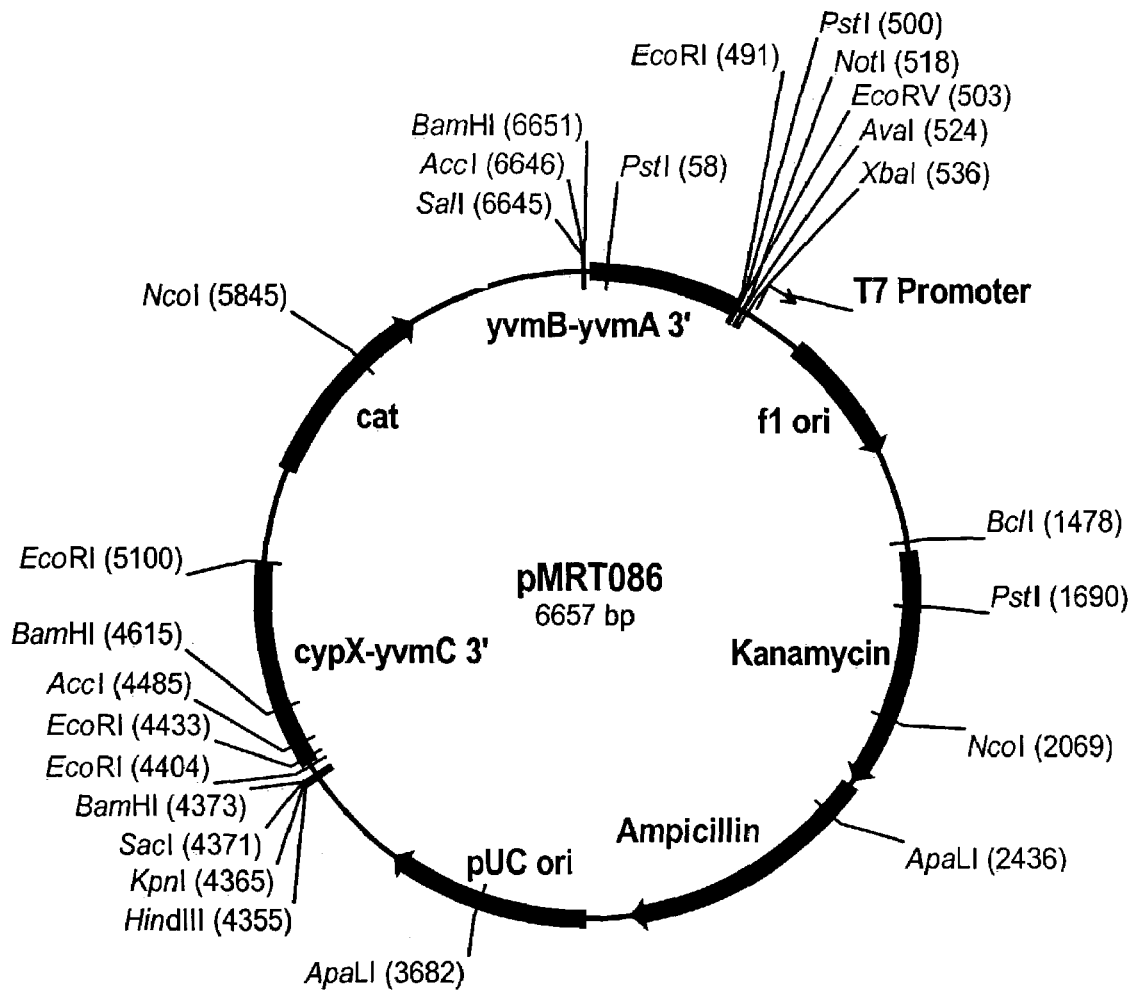
FIG. 6 shows a restriction map of pMRT086.

DNA sequence comparison of the cypX-yvmC and yvmB-yvmA operons amplified from *Bacillus subtilis* BRG1 cloned into plasmid pMRT084 and the published sequence of *Bacillus subtilis* 168 (Kunst et al., 1997, *Nature* 390:249-256) shows that these sequences are identical. In order to create a *Bacillus subtilis* strain deleted at these operons, plasmid pMRT084 was digested with BsgI to delete most of the cypX-yvmC and yvmB-yvmA operons, leaving about 500 bases at each end. The digested BsgI DNA was treated with T4 DNA polymerase and shrimp alkaline phosphatase (SAP) according to the manufacturer's instructions (Roche Diagnostics Corporation, Indianapolis, Ind.). Plasmid pECC1 (Youngman et al., 1984, *Plasmid* 12: 1-9) was digested with SmaI. A fragment of approximately 5100 bp from pMRT084 and a fragment of approximately 1600 bp fragment from pECC1 which contains the chloramphenicol resistance gene (cat) were isolated from a 0.8% agarose-0.5× TBE gel using the QIAquick DNA Extraction Kit (QIAGEN, Inc., Valencia, Calif.) according to the manufacturer's instructions, ligated, and used to transform *E. coli* XL1 Blue cells according to the manufacturer's instructions (Stratagene, Inc., La Jolla, Calif.). Transformants were selected on 2× YT agar plates supplemented with 100 µg of ampicillin per ml. Transformants carrying the correct plasmid with most of the cypX-yvmC and yvmB-yvmA operons deleted were identified by PCR amplification using primers 19 and 20. PCR amplification was conducted in 50 µl reactions composed of 1 ng of plasmid DNA, 0.4 µM of each primer, 200 µM each of dATP, dCTP, dGTP, and dTTP, 1× PCR Buffer II (Applied Biosystems, Inc., Foster City, Calif.) with 2.5 mM $MgCl_2$, and 2.5 units of AmpliTaq Gold™ DNA polymerase (Applied Biosystems, Inc., Foster City, Calif.). The reactions were performed in a RoboCycler 40 thermacycler programmed for 1 cycle at 95° C. for 10 minutes; 25 cycles each at 95° C. for 1 minute, 55° C. for 1 minute, and 72° C. for 1 minute; and 1 cycle at 72° C. for 7 minutes. The PCR product was visualized using a 0.8% agarose-0.5× TBE gel. This construct was designated pMRT086 (FIG. 6).

```
Primer 19:
5'-TAGACAATTGGAAGAGAAAAGAGATA-3'   (SEQ ID NO: 27)

Primer 20:
5'-CCGTCGCTATTGTAACCAGT-3'         (SEQ ID NO: 28)
```

Plasmid pMRT086 was linearized with ScaI and transformed into *Bacillus subtilis* RB128 competent cells in the presence of 0.2 μg of chloramphenicol per ml. Transformants were selected on Tryptose blood agar base (TBAB) plates containing 5 μg of chloramphenicol per ml, and grown at 37° C. for 16 hours. Chromosomal DNA was prepared from several transformants using a QIAGEN tip-20 column according to the manufacturer's instructions. Chloramphenicol resistant colonies were screened by PCR for deletion of the cypX-yvmC and yvmB-yvmA operons via PCR using primers 3 and 19, 3 and 20, 4 and 19, and 4 and 20. PCR amplification was conducted in 50 μl reactions composed of 200 ng of chromosomal DNA, 0.4 μM of each primer, 200 μM each of dATP, dCTP, dGTP, and dTTP, 1× PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 10 minutes; 25 cycles each at 95° C. for 1 minute, 55° C. for 1 minute, and 72° C. for 1 minute; and 1 cycle at 72° C. for 7 minutes. The PCR products were visualized using a 0.8% agarose-0.5× TBE gel. The resulting *Bacillus subtilis* RB128 cypX-yvmC and yvmB-yvmA deleted strain was designated *Bacillus subtilis* MaTa17.

*Bacillus subtilis* MaTa17 was submitted for fermentation using the same medium and conditions as described in Example 1. No observable red pigment was produced by *Bacillus subtilis* strain MaTa17 after 48 hours. Moreover, the second DNA microarray analysis in Example 1 identified the cypX-yvmC operon as the only operon involved in synthesis of the red pigment and Examples 3 and 4 below show that deletion of the cypX or the yvmC gene is necessary for elimination of the red pigment. Thus, in order to test the usefulness of the elimination of the red pigment, the cypX gene was deleted in various *Bacillus subtilis* strains such as *Bacillus subtilis* A164Δ5 (U.S. Pat. No. 5,891,701), *Bacillus subtilis* RB194, and *Bacillus subtilis* RB197 (WO 03/054163) as well as in other *Bacillus* strains as described herein where elimination of the red pigment would be beneficial in product recovery.

Example 3

Construction of *Bacillus subtilis* Strain A164Δ5ΔcypX

In order to verify the role the cypX gene plays in the synthesis of the red pigment, the cypX gene was deleted from *Bacillus subtilis* A164Δ5 (U.S. Pat. No. 5,891,701). Plasmid pMRT122 (WO 03/054163) was used to transform *Bacillus subtilis* A164Δ5 competent cells. Transformants were selected on TBAB-agar plates supplemented with 1 μg of erythromycin and 25 μg of lincomycin per ml and incubated at 30° C. for 24-48 hours. The deleted cypX gene was introduced into the chromosome of *Bacillus subtilis* A164Δ5 via Campbell-type integration by incubating a freshly streaked plate of *Bacillus subtilis* A164Δ5 (pMRT122) cells at 45° C. for 16 hours and selecting for healthy growing colonies resulting in *Bacillus subtilis* strain A165Δ5::pMRT122. Several of the healthy growing colonies were inoculated into 1 ml of LB broth and incubated at 30° C., 250 rpm overnight. The cultured cells were serially passaged at least three times using 10 μl of cultured cells. After the last passage, cultured cells were streaked onto LB agar plates for isolation and incubated at 37° C., for 16 hours. Individual colonies were picked onto LB agar and TBAB plates supplemented with 1 μg of erythromycin and 25 μg of lincomycin per ml in replicate fashion and grown at 37° C. for 16 hours. Chromosomal DNA from potential integrants was isolated using the REDextract-N-Amp™ Plant PCR kits (Sigma Chemical Company, St. Louis, Mo.) as follows: Single Bacillus colonies were inoculated into 100 μl of Extraction Solution (Sigma Chemical Company, St. Louis, Mo.), incubated at 95° C. for 10 minutes, and then diluted with an equal volume of Dilution Solution (Sigma Chemical Company, St. Louis, Mo.). PCR was performed using 4 μl of extracted DNA in conjunction with the REDextract-N-Amp PCR Reaction Mix and primers 12 and 21 according to the manufacturer's instructions. PCR reactions were performed in a RoboCycler 40 thermacycler programmed for 1 cycle at 95° C. for 9 minutes; 3 cycles each at 95° C. for 1 minute, 52° C. for 1 minute, and 72° C. for 1 minute; 27 cycles each at 95° C. for 1 minute, 55° C. for 1 minute, and 72° C. for 1 minute; and 1 cycle at 72° C. for 5 minutes. The PCR product was visualized in a 0.8% agarose-0.5× TBE gel. The resulting strain was designated *Bacillus subtilis* A164Δ5ΔcypX. The presence or loss of red pigment in *Bacillus subtilis* was visualized on Spizizen's minimal salts-agar (SMS) plates (Anagnostopoulos and Spizizen, 1961, supra) supplemented per liter with 0.5% sucrose, 0.15 mg of biotin, 24 mg of ferric sulfate, 9.6 mg of manganese sulfate, 3 mg of copper sulfate, 6 mg of zinc chloride, and 0.06% citric acid. *Bacillus subtilis* A164Δ5ΔcypX appeared to be colorless when compared to *Bacillus subtilis* A164Δ5.

```
Primer 21:
5'-CATGGGAGAGACCTTTGG-3'  (SEQ ID NO: 29)
```

Example 4

Construction of Strain *Bacillus subtilis* A164Δ5ΔyvmC

Figure 7:
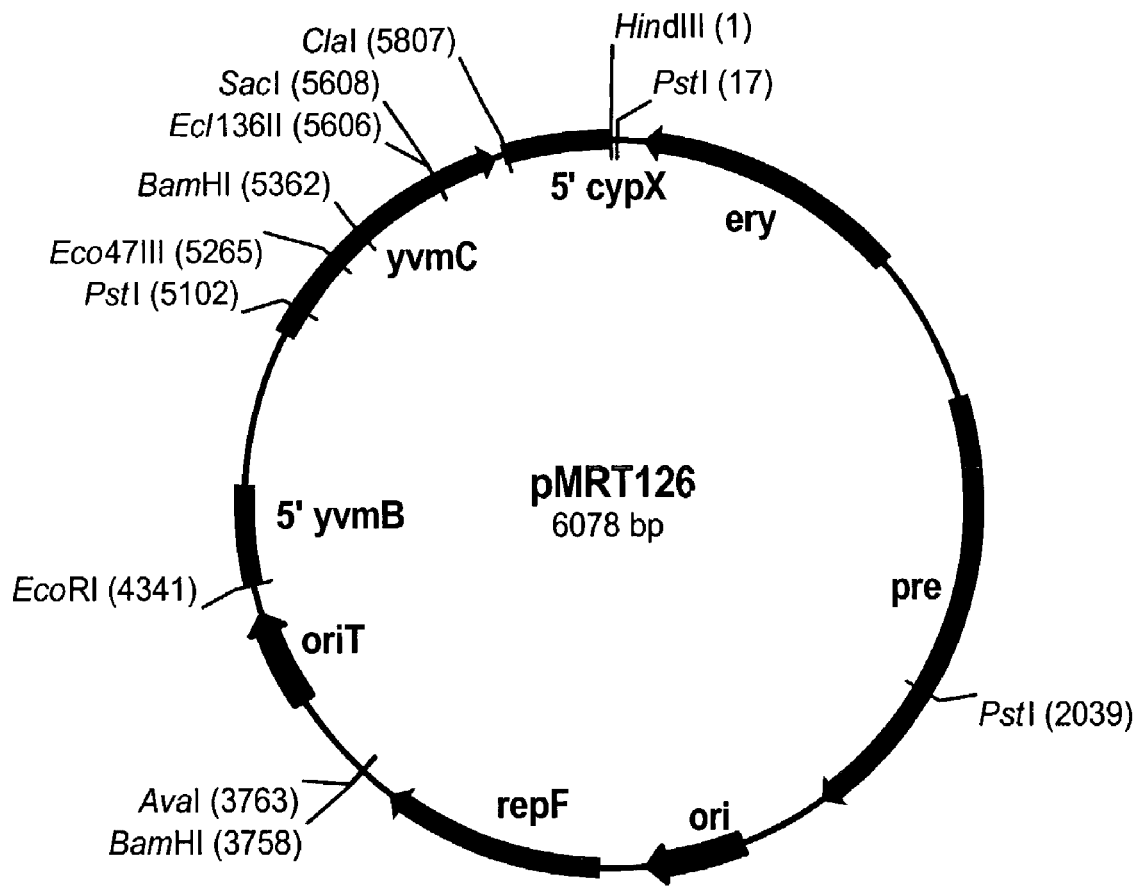
FIG. 7 shows a restriction map of pMRT126.

In order to validate if cypX and/or yvmC are responsible for the synthesis of the red pigment, the yvmC gene was deleted, leaving the cypX gene intact. Plasmids pMRT074 (WO 03/054163) and pMRT084 were digested with EcoRI and HindIII. A fragment of approximately 4300 bp from pMRT074 and a fragment of approximately 1700 bp from pMRT084 were isolated from a 0.8% agarose-0.5× TBE gel using a QIAquick DNA purification kit according to the manufacturer's instructions, ligated and used to transform *Bacillus subtilis* 168Δ4 competent cells. Transformants were selected on TBAB-agar plates supplemented with 1 μg of erythromycin and 25 μg of lincomycin per ml and incubated at 30° C. for 24 hours. Transformants carrying the correct plasmid were identified on a 0.8% agarose-0.5× TBE gel by restriction analysis with DraI. The resulting construct was designated pMRT126 (FIG. 7).

Figure 8:
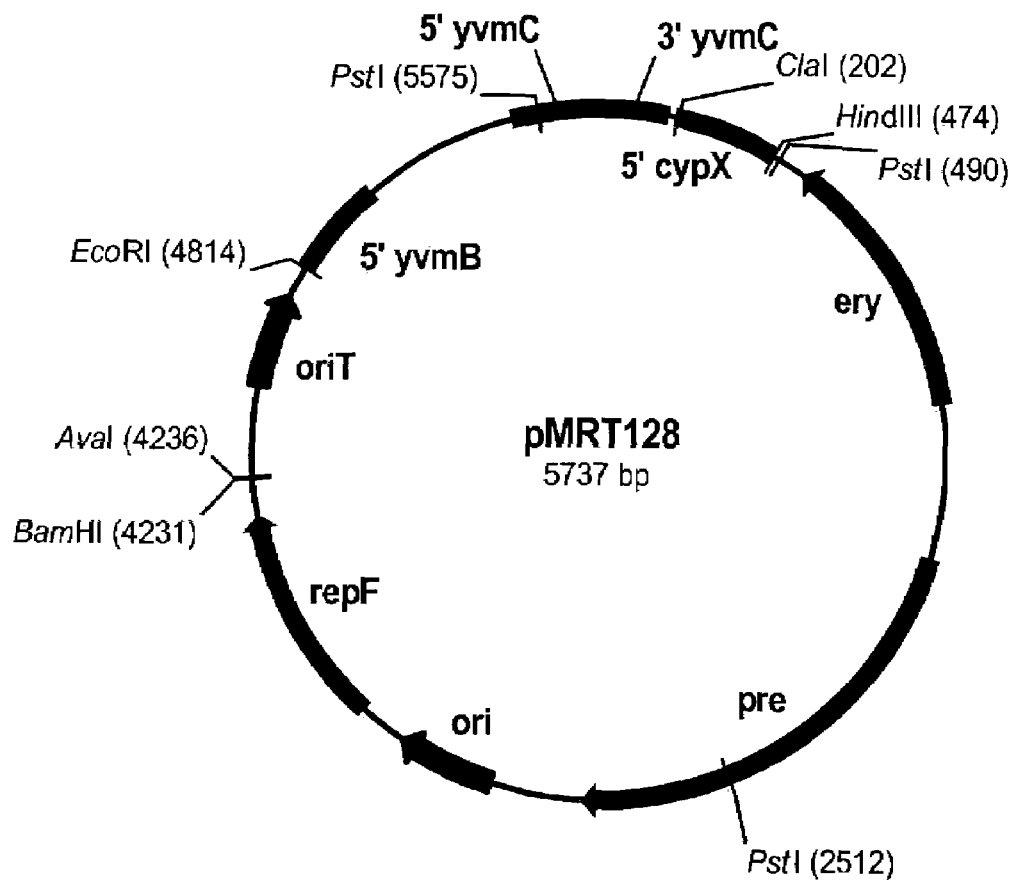
FIG. 8 shows a restriction map of pMRT128.

Plasmid pMRT126 was digested with Ecl136II/Eco47III to make a deletion in the yvmC gene, ligated and used to transform *Bacillus subtilis* 168Δ4. Transformants were selected on TBAB-agar plates supplemented with 1 μg of erythromycin and 25 μg of lincomycin per ml and incubated at 30° C. for 24 hours. Transformants carrying the correct plasmid were identified on a 2% agarose-0.5× TBE gel by restriction analysis with DraI. The resulting plasmid was designated pMRT128 (FIG. 8).

Plasmid pMRT128 was used to transform *Bacillus subtilis* A164Δ5 competent cells. Transformants were selected on TBAB-agar plates supplemented with 1 μg of erythromycin and 25 μg of lincomycin per ml and incubated at 30° C. for 24-48 hours. The deleted yvmC gene was introduced into the chromosome of *Bacillus subtilis* A164Δ5 via Campbell-type integration by incubating a freshly streaked plate of *Bacillus* subtilis A164Δ5 (pMRT128) cells at 45° C. for 16 hours and selecting for healthy growing colonies. Several of the healthy growing colonies were inoculated into 1 ml of LB broth and incubated at 30° C., 250 rpm overnight. The cultured cells were serially passaged at least three times using 10 µl of cultured cells. After the last passage, cultured cells were streaked onto LB agar plates for isolation and incubated at 37° C., for 16 hours. Individual colonies were picked onto LB agar, TBAB plates supplemented with 1 µg of erythromycin and 25 µg of lincomycin per ml, and SMS plates containing trace metals described in Example 3, in replicate fashion, and grown at 37° C. for 16-48 hours. Chromosomal DNA from erythromycin sensitive colonies was isolated using the REDextract-N-Amp™ Plant PCR kits as described in Example 3, and screened by PCR for the deleted yvmC gene with primers 7 and 10 using PCR cycling conditions described in Example 3. PCR products were visualized in a 0.8% agarose-0.5× TBE gel. The presence or loss of the red pigment in Bacillus subtilis was visualized on the Spizizen's minimal salts-agar (SMS) plates containing trace metals. The yvmC-deleted strain appeared to be colorless when compared to wild-type strains, and was designated Bacillus subtilis A164Δ5ΔyvmC.

Example 5

Fermentations of Bacillus subtilis Strains

Bacillus subtilis strains RB187, RB194 and RB197, constructed as described in WO 03/054163, were cultivated in a 3 liter fermentor containing 1.5 liters of minimal salts medium composed per liter of 6.5 g of KH$_2$PO$_4$, 4.5 g of Na$_2$HPO$_4$, 3.0 g of (NH$_4$)$_2$SO$_4$, 2.0 g of sodium citrate, 3.0 g of MgSO$_4$.7H$_2$O, 0.15 g of biotin, 15 g of saccharide, 0.5 g of CaCl$_2$.2H$_2$O, and trace elements. The fermentation was fed with saccharide at a rate of 2 g of saccharide/liter/hour. The cultures were sparged with air at 1 to 2 liters per minute and agitated at 1250 rpm. The fermentations were maintained at a pH of 7.0±0.2 and a temperature of 32-37° C. The production of red pigment was visible by 12 hours in the whole broth supernatant and cell pellet, and intensified for the remainder of the fermentation, up to 48 hours with Bacillus subtilis strain RB187. No visible production of red pigment was observed with Bacillus subtilis strains RB194 and RB197. Table 1 summarizes the results for the strains evaluated for red pigment synthesis in this invention.

TABLE 1

Summary of strains evaluated for red pigment synthesis

| Strain | Reference | Gene deletion | Red pigment |
|---|---|---|---|
| Bacillus subtils MaTa17 | Example 2 | cypX, yvmC, yvmA and yvmB | No |
| Bacillus subtilis RB187 | WO 03/054163 | None | Yes |
| Bacillus subtilis RB194 | WO 03/054163 | cypX, yvmC, yvmA and yvmB | No |
| Bacillus subtilis RB197 | WO 03/054163 | cypX | No |
| Bacillus subtilis A164Δ5ΔcypX | Example 3 | cypX | No |
| Bacillus subtilis A164Δ5ΔyvmC | Example 4 | yvmC | No |
| Bacillus licheniformis SJ1904ΔcypX | Example 6 | cypX | No |

Example 6

Construction of Strain Bacillus licheniformis SJ1904ΔcypX

The cypX gene from Bacillus licheniformis SJ1904 (U.S. Pat. No. 5,733,753) was PCR amplified with primers 22 and 23.

Primer 22:
5'-GAATTCGCAGGAGGAACGAGTATG-3' (SEQ ID NO: 30)

Primer 23:
5'-AAGCTTGAAGATCAGTGAGGCAGC-3' (SEQ ID NO: 31)

Figure 9:
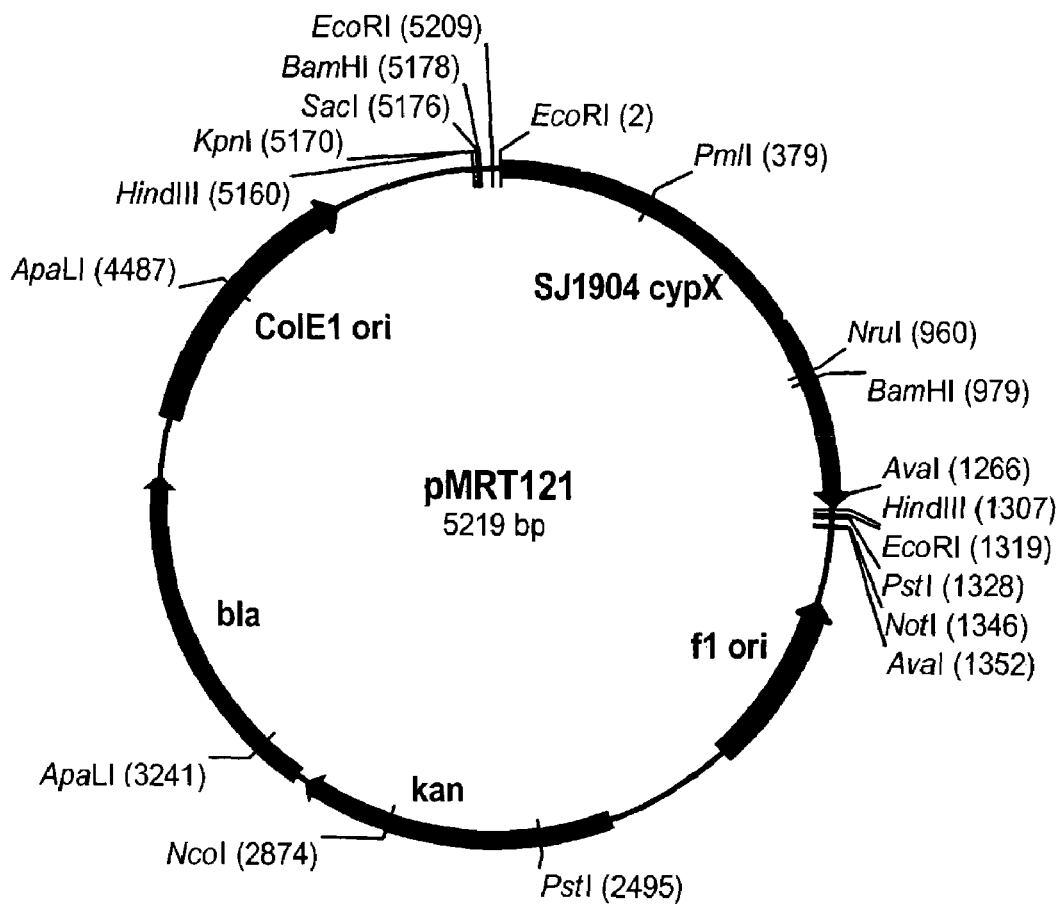
FIG. 9 shows a restriction map of pMRT121.

The amplification reactions (50 µl) were composed of 200 ng of Bacillus licheniformis SJ1904 chromosomal DNA, 0.4 µM each of primers 22 and 23, 200 µM each of dATP, dCTP, dGTP, and dTTP, 1× Expand™ High Fidelity buffer with 1.5 mM MgCl$_2$, and 2.6 units of Expand™ High Fidelity PCR System enzyme mix (Roche Diagnostic Corporation, Indianapolis, Ind.). Bacillus licheniformis SJ1904 chromosomal DNA was obtained using a QIAGEN tip-20 column according to the manufacturer's instructions. Amplification reactions were performed in a RoboCycler 40 thermacycler programmed for 1 cycle at 94° C. for 2 minutes; 30 cycles each at 94° C. for 1 minute, 52° C. for 1 minute, and 68° C. for 2 minutes, followed by 1 cycle at 72° C. for 7 minutes. Reaction products were analyzed by agarose gel electrophoresis using a 0.8% agarose-0.5× TBE gel. The resulting fragment (approximately 1300 bp) comprising the cypX gene was cloned into pCR2.1 using the TA-TOPO Cloning Kit and used to transform E. coli OneShot™ cells according to the manufacturer's instructions. Transformants were selected on 2× YT agar plates supplemented with 100 µg of ampicillin per ml. Plasmid DNA from several transformants was isolated using QIAGEN tip-20 columns according to the manufacturer's instructions and verified by DNA sequencing with M13 (-20) forward and M13 reverse primers. The resulting plasmid was designated pMRT121 (FIG. 9).

Figure 10:
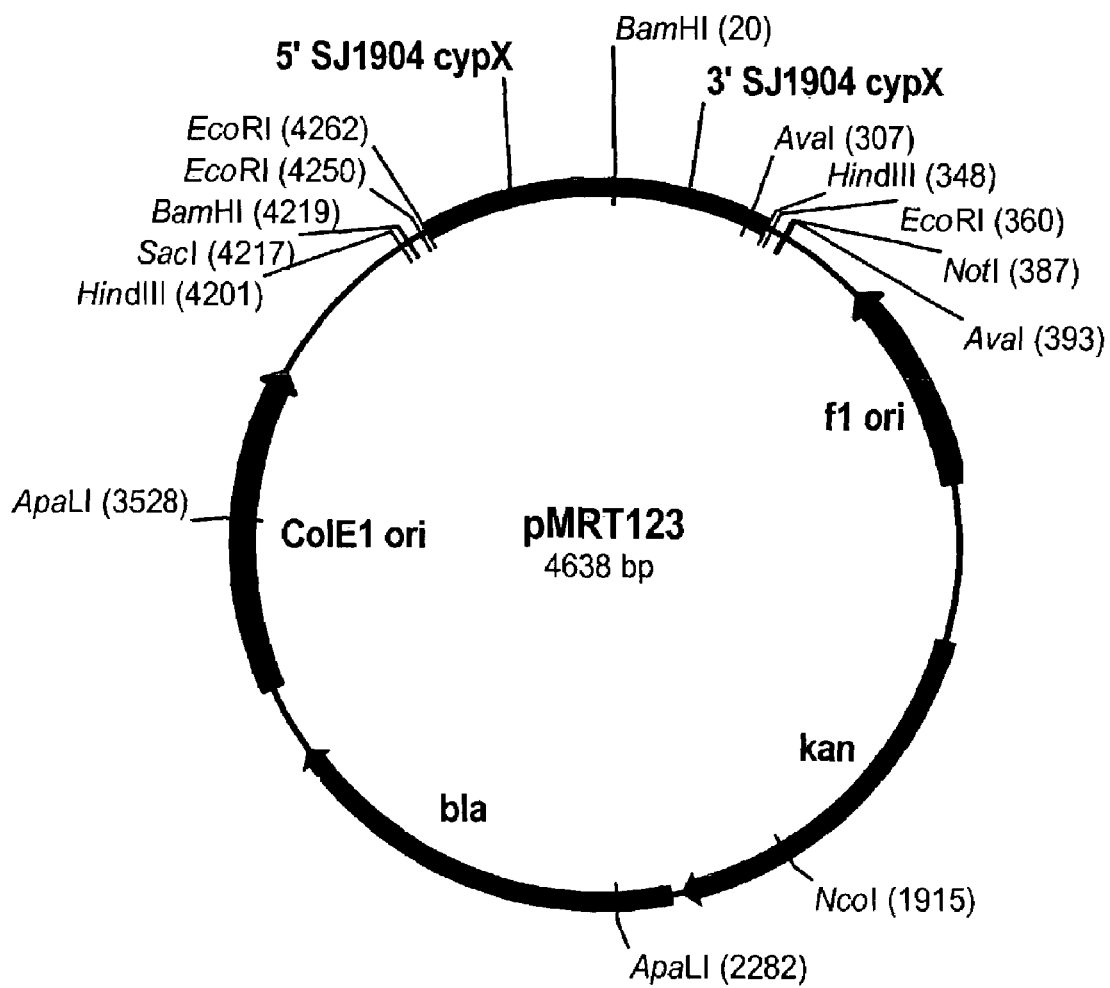
FIG. 10 shows a restriction map of pMRT123.

Plasmid pMRT121 was digested with NruI and PmlI to make a deletion in the cypX gene leaving about 350 bp at each end, ligated, and used to transform E. coli XL1 Blue cells according to the manufacturer's instructions. Transformants were selected on 2×YT agar plates supplemented with 100 µg of ampicillin per ml and incubated at 37° C. for 16 hours. Transformants carrying the correct plasmid were identified on a 2% agarose-0.5× TBE gel by restriction analysis with DraI. The resulting plasmid was named pMRT123 (FIG. 10).

Figure 11:
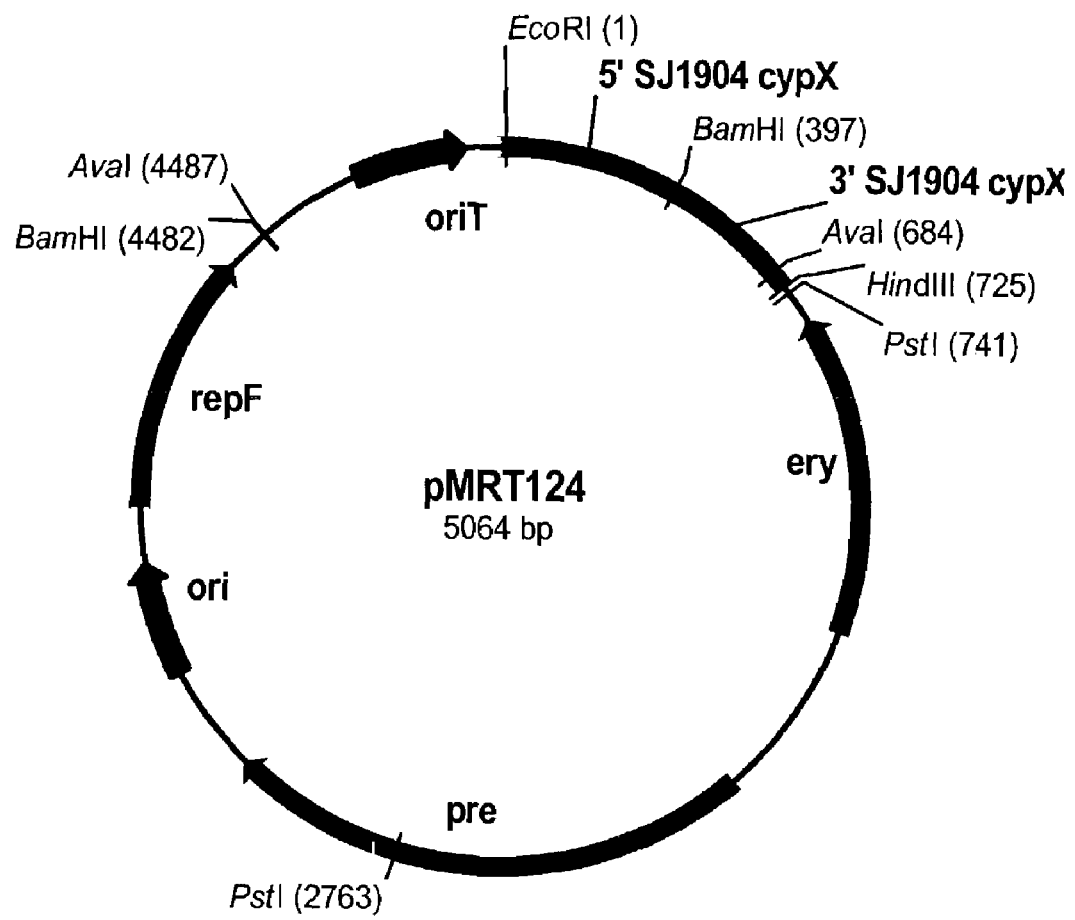
FIG. 11 shows a restriction map of pMRT124.

Plasmids pMRT074 and pMRT123 were digested with EcoRI and HindIII. A fragment of approximately 700 bp from pMRT123 and a fragment of approximately 4300 bp from pMRT074 were isolated from a 0.8% agarose-0.5× TBE gel using a QIAquick DNA purification kit according to the manufacturer's instructions, ligated, and used to transform Bacillus subtilis A168Δ4 competent cells. Transformants were selected on TBAB-agar plates supplemented with 1 µg of erythromycin and 25 µg of lincomycin per ml and incubated at 30° C. for 24 hours. Transformants carrying the correct plasmid were identified on a 2% agarose-0.5× TBE gel by restriction analysis with DraI. The resulting construct was designated pMRT124 (FIG. 11).

Plasmid pMRT124 was used to transform *Bacillus licheniformis* SJ1904 electrocompetent cells according to the method described by Xue et al., 1999, *Journal of Microbiological Methods* 34:183-191. After electroporation, cells were incubated in LBSM medium (Luria-Bertani medium containing 0.5 M sorbitol and 0.38 M mannitol) supplemented with 0.2 µg/ml erythromycin for 2.5 to 3 hours, plated on TBAB-agar plates supplemented with 1 µg of erythromycin and 25 µg of lincomycin per ml and incubated at 30° C. for 24-48 hours. The deleted cypX gene in plasmid pMRT124 was introduced into the *B. licheniformis* SJ1904 chromosome via Campbell-type integration by incubating a freshly streaked plate of *Bacillus licheniformis* A164Δ5 (pMRT124) cells at 50° C. for 16 hours and selecting for healthy growing colonies. Several of the healthy growing colonies were inoculated into 1 ml of LB broth and incubated at 30° C., 250 rpm overnight. The cultured cells were serially passaged at least three times using 10 µl of cultured cells. After the last passage, cultured cells were streaked onto LB agar plates for isolation and incubated at 37° C., for 16 hours. Individual colonies were picked onto LB agar and TBAB plates supplemented with 1 µg of erythromycin and 25 µg of lincomycin per ml in replicate fashion and grown at 37° C. for 16 hours. Chromosomal DNA from erythromycin sensitive colonies was isolated using the REDextract-N-Amp™ Plant PCR kits as described in Example 3, and screened by PCR for the deleted cypX gene with primers 22 and 23 using PCR cycling conditions are described in Example 3. PCR products were visualized in a 0.8% agarose-0.5× TBE gel. The resulting strain was designated *Bacillus licheniformis* SJ1904ΔcypX. The presence or loss of the red pigment formation by *Bacillus licheniformis* was visualized by streaking *Bacillus licheniformis* SJ1904 and *B. licheniformis* SJ1904ΔcypX side-by-side on the Spizizen's minimal salts-agar (SMS) plates supplemented with trace metals (Example 3). Plates were incubated at 37° C. for 48 hours. The cypX-deleted strain appeared to be colorless when compared to the control strain, indicating that loss of red pigment formation was accomplished by deleting the cypX gene.

Example 7

Isolation of Red Pigment from RB187 Supernatant

The red pigment found in the broth of strain *Bacillus subtilis* RB187 was isolated by adjusting 40 ml of supernatant to pH 1.5 with 6 N HCl. The acidified broth was incubated at 94° C. for 30 minutes and the pigment was pelleted by centrifugation in a SORVALL 6000B centrifuge at 2500 rpm, 4° C. for 20 minutes (SORVALL, Inc., Newtown, Conn.). The red pellet was washed by centrifugation three times with 20 ml HPLC-grade water, dissolved in 10 ml alkaline methanol and recovered by acidification to pH 1.5 in the presence of excess ferric chloride as described by Canale-Parola, 1963, Archiv für Mikrobiologie 46: 414-427. Spectral analysis of the red pigment in 2 M NaOH from 600 nm to 200 nm yields an absorption spectrum with peaks at 242 nm, 280 nm and 242 nm. This UV-visible spectrum of the purified pigment is similar to the pulcherrimin absorption spectrum found by Canale-Parola. Collectively, the solubility in alkaline methanol, insolubility in acid, and characteristic absorbance spectrum strongly suggest that the red pigment is pulcherrimin.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method of producing a heterologous protein, comprising:
   (a) cultivating a mutant *Bacillus subtilis* cell transformed with a nucleic acid construct comprising a nucleic acid directing synthesis of the heterologous protein in a medium suitable for the production of the heterologous protein, wherein the mutant cell comprises a deletion mutation in a cypX gene comprising SEQ ID NO: 1, a yvmC gene comprising SEQ ID NO: 7, or both genes, in which the deletion mutation(s) renders the cell deficient in red pigment compared to a wild-type *Bacillus subtilis* cell comprising the cypX gene comprising SEQ ID NO: 1, the yvmC gene comprising SEQ ID NO: 7, or both genes; and
   (b) recovering the heterologous protein from the cultivation medium.

2. The method of claim 1, wherein the heterologous protein is involved in the biosynthesis of a biopolymer.

3. The method of claim 1, wherein the heterologous protein is involved in the biosynthesis of a metabolite.

4. The method of claim 1, wherein the mutant cell produces no detectable red pigment compared to the parent *Bacillus subtilis* cell when cultured under identical conditions.

5. A isolated mutant *Bacillus subtilis* cell, comprising a deletion mutation in a cypX gene comprising SEQ ID NO: 1, a yvmC gene comprising SEQ ID NO: 7, or both genes, in which the deletion mutation(s) renders the cell deficient in red pigment compared to a wild-type *Bacillus subtilis* cell comprising the cypX gene comprising SEQ ID NO: 1, the yvmC gene comprising SEQ ID NO: 7, or both genes, transformed with a nucleic acid construct comprising a nucleic acid directing synthesis of the heterologous protein.

6. The mutant cell of claim 5, wherein the heterologous protein is involved in the biosynthesis of a biopolymer.

7. The mutant cell of claim 5, wherein the heterologous protein is involved in the biosynthesis of a metabolite.

8. The mutant cell of claim 5, which produces no detectable red pigment compared to the parent *Bacillus subtilis* cell when cultured under identical conditions.

9. A method of producing a an isolated mutant *Bacillus subtilis* cell, comprising: making a deletion mutation in a cypX gene comprising SEQ ID NO: 1, a yvmC gene comprising SEQ ID NO: 7, or both genes, of a *Bacillus subtilis* cell, in which the deletion mutation(s) renders the cell deficient in red pigment compared to a wild-type *Bacillus subtilis* cell comprising the cypX gene comprising SEQ ID NO: 1, the yvmC gene comprising SEQ ID NO: 7, or both genes, and transforming the cell with a nucleic acid construct comprising a nucleic acid directing synthesis of a heterologous protein.

10. The method of claim 9, wherein the heterologous protein is involved in the biosynthesis of a biopolymer.

11. The method of claim 9, wherein the heterologous protein is involved in the biosynthesis of a metabolite.

12. The method of claim 1, wherein the mutant cell is further deficient in the production of protease.

13. The method of claim 1, wherein the mutant cell is further deficient in the production of surfactin.

14. The mutant cell of claim 5, which is further deficient in the production of protease.

15. The mutant cell of claim 5, which is further is deficient in the production of surfactin.

16. The method of claim 9, wherein the mutant cell produces no detectable red pigment when compared to the parent *Bacillus subtilis* cell when cultured under identical conditions.

17. The method of claim 9, wherein the mutant *Bacillus subtilis* cell is further deficient in the production of protease.

18. The method of claim 9, wherein the mutant *Bacillus subtilis* cell is further-deficient in the production of surfactin.

19. The method of claim 1, wherein the mutant *Bacillus subtilis* cell does not produce spores.

20. The mutant cell of claim 5, which does not produce spores.

21. The method of claim 9, wherein the mutant *Bacillus subtilis* cell does not produce spores.

22. The method of claim 1, wherein the mutant *Bacillus subtilis* cell is further deficient in the production of amylase.

23. The mutant cell of claim 5, which is further deficient in the production of amylase.

24. The method of claim 9, wherein the mutant *Bacillus subtilis* cell is further deficient in the production of amylase.

* * * * *

SEQUENCE LISTING

```
<160> NUMBER OF SEQ ID NOS: 31

<210> SEQ ID NO 1
<211> LENGTH: 1215
<212> TYPE: DNA
<213> ORGANISM: Bacillus subtilis

<400> SEQUENCE: 1
atgagccaat cgattaaatt gtttagtgtg ctttctgatc aatttcaaaa caatccatat      60
gcttattttt cacaactgcg ggaggaagat ccggttcatt atgaagagtc gatagacagt     120
tattttatca gccgctatca tgatgtccgc tatatccttc agcatccgga tatcttcacg     180
acgaaatcac ttgttgagcg tgccgaacca gtcatgcgag gccctgtgct ggcccaaatg     240
catggaaaag aacactctgc caaagaaga attgtagtga aagctttat cggtgacgca       300 ctggatcatc tgtctccatt gattaaacaa aatgcagaaa acttgttagc gccttatctt     360
gaaagaggga aaagtgatct cgtcaatgat tttggaaaga cgtttgcggt gtgcgtcacg     420
atggacatgc tcgggctgga taaaagagac catgaaaaaa tctctgagtg gcacagcgga     480
gttgccgatt ttatcacgag tatctctcaa tctcctgaag cgcgggcaca ttcgttatgg     540
```

```
tgcagcgaac agctttccca atacttgatg ccggtcatta aagaacgtcg cgtcaatccg    600
ggatcagatt taatttcgat cctatgtact tctgaatatg aaggcatggc gctgtcggac    660
aaggatatac tcgcactgat tcttaatgtg ctgttagccg caacggaacc ggctgataag    720
acgctggcac tgatgatcta ccatttgctc aacaatcctg agcagatgaa tgatgttttg    780
gctgaccgtt cgttagttcc gagagccatt gcggagacat tgcgttataa accgccggtt    840
cagctgattc cgcggcagct gtcccaagat acagtggtcg gcggtatgga aatcaaaaaa    900
gatacgattg ttttttgtat gatcggtgcg gctaaccggg accctgaagc atttgaacag    960
cctgacgtgt ttaatattca tcgggaagat cttggtatca agagcgcttt tagcggcgcc   1020
gcccggcatc tcgctttcgg atccggcatt cataactgtg taggagcagc ttttgccaaa   1080
aacgaaatcg aaattgtagc taatattgtg ctggataaga tgcggaatat cagattagag   1140
gaagattttt gttatgctga gtccggtctg tatacacgcg gacctgtttc acttctcgtt   1200
gcgtttgacg gggca                                                    1215

<210> SEQ ID NO 2
<211> LENGTH: 405
<212> TYPE: PRT
<213> ORGANISM: Bacillus subtilis

<400> SEQUENCE: 2

Met Ser Gln Ser Ile Lys Leu Phe Ser Val Leu Ser Asp Gln Phe Gln
1               5                   10                  15

Asn Asn Pro Tyr Ala Tyr Phe Ser Gln Leu Arg Glu Glu Asp Pro Val
            20                  25                  30

His Tyr Glu Glu Ser Ile Asp Ser Tyr Phe Ile Ser Arg Tyr His Asp
        35                  40                  45

Val Arg Tyr Ile Leu Gln His Pro Asp Ile Phe Thr Thr Lys Ser Leu
    50                  55                  60

Val Glu Arg Ala Glu Pro Val Met Arg Gly Pro Val Leu Ala Gln Met
65                  70                  75                  80

His Gly Lys Glu His Ser Ala Lys Arg Arg Ile Val Val Arg Ser Phe
                85                  90                  95

Ile Gly Asp Ala Leu Asp His Leu Ser Pro Leu Ile Lys Gln Asn Ala
            100                 105                 110

Glu Asn Leu Leu Ala Pro Tyr Leu Glu Arg Gly Lys Ser Asp Leu Val
        115                 120                 125

Asn Asp Phe Gly Lys Thr Phe Ala Val Cys Val Thr Met Asp Met Leu
    130                 135                 140

Gly Leu Asp Lys Arg Asp His Glu Lys Ile Ser Glu Trp His Ser Gly
145                 150                 155                 160

Val Ala Asp Phe Ile Thr Ser Ile Ser Gln Ser Pro Glu Ala Arg Ala
                165                 170                 175

His Ser Leu Trp Cys Ser Glu Gln Leu Ser Gln Tyr Leu Met Pro Val
            180                 185                 190

Ile Lys Glu Arg Arg Val Asn Pro Gly Ser Asp Leu Ile Ser Ile Leu
        195                 200                 205

Cys Thr Ser Glu Tyr Glu Gly Met Ala Leu Ser Asp Lys Asp Ile Leu
    210                 215                 220

Ala Leu Ile Leu Asn Val Leu Leu Ala Ala Thr Glu Pro Ala Asp Lys
225                 230                 235                 240

Thr Leu Ala Leu Met Ile Tyr His Leu Leu Asn Asn Pro Glu Gln Met
```

```
                 245              250                 255
Asn Asp Val Leu Ala Asp Arg Ser Leu Val Pro Arg Ala Ile Ala Glu
            260                 265                 270
Thr Leu Arg Tyr Lys Pro Pro Val Gln Leu Ile Pro Arg Gln Leu Ser
        275                 280                 285
Gln Asp Thr Val Val Gly Gly Met Glu Ile Lys Lys Asp Thr Ile Val
    290                 295                 300
Phe Cys Met Ile Gly Ala Ala Asn Arg Asp Pro Glu Ala Phe Glu Gln
305                 310                 315                 320
Pro Asp Val Phe Asn Ile His Arg Glu Asp Leu Gly Ile Lys Ser Ala
                325                 330                 335
Phe Ser Gly Ala Ala Arg His Leu Ala Phe Gly Ser Gly Ile His Asn
            340                 345                 350
Cys Val Gly Ala Ala Phe Ala Lys Asn Glu Ile Glu Ile Val Ala Asn
        355                 360                 365
Ile Val Leu Asp Lys Met Arg Asn Ile Arg Leu Glu Glu Asp Phe Cys
    370                 375                 380
Tyr Ala Glu Ser Gly Leu Tyr Thr Arg Gly Pro Val Ser Leu Leu Val
385                 390                 395                 400
Ala Phe Asp Gly Ala
            405

<210> SEQ ID NO 3
<211> LENGTH: 1218
<212> TYPE: DNA
<213> ORGANISM: Bacillus subtilis

<400> SEQUENCE: 3
gtgtacactt tggctcatac aaaatcaaag gcagtattga tcttatacac tgtttgcttc     60
agtgcatttt ttgcatcttt aagccagaac atttattcac ctattcttcc gatcattaaa    120
gaatcattcc atgtttccac agctatggtg aacctgtcag tctcagtttt tatgattgtg    180
acagcaataa tgcaaattat attaggagcg atcattgatt ttaaaggcgc tcggatcgtc    240
ttgattaccg gtattctggc aacggcagca gccagcatcg gctgtgcggt gactactgac    300
tttaccttgt ttctgatatt cagaatgata caggcagccg gttccgcagc actgcctctt    360
attgctgcca caacgatcgg acagctgttt acaggaaatg aacgcgggag tgcaatggga    420
acgtatcaaa tgctcctgtc tgtcgcaccg gctattgctc cagttctagg aggattcata    480
ggcggagcag ccggatacga agggattttt tggatacttg cggccatctc tatcgttttg    540
ctggtgacaa acagcatcac ctttcctaaa gattctccaa ctgaatctat gcagcaagcc    600
aaaggcaatg tgttcgctca ttataaatca atatttacaa atcgaacagg gaacgtcatt    660
ttgactttaa gttttgttct cttttttcatt tattttgcag taattgtcta cctcccaata    720
ttgctgacag agcattacca tatagatgtg ggtatagcag gactgttata tttgccgctg    780
gcgctgagca cgattgcagg tacgtttctg tttaaaagaa tacaggcaaa aatcgggctg    840
cacaccttgt ttatcggaag caatgtgatt gccgcctgca gcatcatttt atttgctgtt    900
acacattccg tttctctcgt tctcatggct ctgacgctgg cactgtttgg catctcgatg    960
ggggttattc ctcccttgta ctctacaatg attactaatg aatttgagca acagagggg   1020
agtgcaatcg gaatgtttaa ctttatccga tatacaggca tggcagcagg tccgatggta   1080
tctgcctact tgctcacaat gatgccgtct gccatgtcct ttagcctcct aggccttgga   1140
tttgccgcat tgagcttttg ccttcttccg ccaatgtttt cgccgcagaa gcgcacgaaa   1200
```

```
caaaaaaagc accacatg                                                     1218
```

<210> SEQ ID NO 4
<211> LENGTH: 406
<212> TYPE: PRT
<213> ORGANISM: Bacillus subtilis

<400> SEQUENCE: 4

```
Met Tyr Thr Leu Ala His Thr Lys Ser Lys Ala Val Leu Ile Leu Tyr
 1               5                  10                  15

Thr Val Cys Phe Ser Ala Phe Phe Ala Ser Leu Ser Gln Asn Ile Tyr
            20                  25                  30

Ser Pro Ile Leu Pro Ile Ile Lys Glu Ser Phe His Val Ser Thr Ala
        35                  40                  45

Met Val Asn Leu Ser Val Ser Val Phe Met Ile Val Thr Ala Ile Met
    50                  55                  60

Gln Ile Ile Leu Gly Ala Ile Ile Asp Phe Lys Gly Ala Arg Ile Val
65                  70                  75                  80

Leu Ile Thr Gly Ile Leu Ala Thr Ala Ala Ser Ile Gly Cys Ala
                85                  90                  95

Val Thr Thr Asp Phe Thr Leu Phe Leu Ile Phe Arg Met Ile Gln Ala
            100                 105                 110

Ala Gly Ser Ala Ala Leu Pro Leu Ile Ala Ala Thr Thr Ile Gly Gln
        115                 120                 125

Leu Phe Thr Gly Asn Glu Arg Gly Ser Ala Met Gly Thr Tyr Gln Met
    130                 135                 140

Leu Leu Ser Val Ala Pro Ala Ile Ala Pro Val Leu Gly Gly Phe Ile
145                 150                 155                 160

Gly Gly Ala Ala Gly Tyr Glu Gly Ile Phe Trp Ile Leu Ala Ala Ile
                165                 170                 175

Ser Ile Val Leu Leu Val Thr Asn Ser Ile Thr Phe Pro Lys Asp Ser
            180                 185                 190

Pro Thr Glu Ser Met Gln Gln Ala Lys Gly Asn Val Phe Ala His Tyr
        195                 200                 205

Lys Ser Ile Phe Thr Asn Arg Thr Gly Asn Val Ile Leu Thr Leu Ser
    210                 215                 220

Phe Val Leu Phe Phe Ile Tyr Phe Ala Val Ile Val Tyr Leu Pro Ile
225                 230                 235                 240

Leu Leu Thr Glu His Tyr His Ile Asp Val Gly Ile Ala Gly Leu Leu
                245                 250                 255

Tyr Leu Pro Leu Ala Leu Ser Thr Ile Ala Gly Thr Phe Leu Phe Lys
            260                 265                 270

Arg Ile Gln Ala Lys Ile Gly Leu His Thr Leu Phe Ile Gly Ser Asn
        275                 280                 285

Val Ile Ala Ala Cys Ser Ile Ile Leu Phe Ala Val Thr His Ser Val
    290                 295                 300

Ser Leu Val Leu Met Ala Leu Thr Leu Ala Leu Phe Gly Ile Ser Met
305                 310                 315                 320

Gly Val Ile Pro Pro Leu Tyr Ser Thr Met Ile Thr Asn Glu Phe Glu
                325                 330                 335

His Asn Arg Gly Ser Ala Ile Gly Met Phe Asn Phe Ile Arg Tyr Thr
            340                 345                 350

Gly Met Ala Ala Gly Pro Met Val Ser Ala Tyr Leu Leu Thr Met Met
        355                 360                 365
```

```
Pro Ser Ala Met Ser Phe Ser Leu Leu Gly Leu Gly Phe Ala Ala Leu
    370                 375                 380

Ser Phe Cys Leu Leu Pro Pro Met Phe Ser Pro Gln Lys Arg Thr Lys
385                 390                 395                 400

Gln Lys Lys His His Met
                405

<210> SEQ ID NO 5
<211> LENGTH: 507
<212> TYPE: DNA
<213> ORGANISM: Bacillus subtilis

<400> SEQUENCE: 5
atgtctgatt tgacaaaaca gatgatatac gacatatacg tgagactgct gcaccttaat      60
gaacaaaaag cgaacacttc acttcagcaa ttttttaagg aggccgcaga agaggatgta     120
gctgaaattc caaaaatat gacaagcatt cacgtcattg actgcatcgg ccagcatgaa      180
cccattaata atgccggaat tgccagaaaa atgaacttat cgaaagcgaa tgtaacgaaa     240
atcagcacaa aactgatcaa ggaagaattc attaacagct atcagctgac agataacaaa     300
aaagaagttt attttaaatt aacccgtaaa ggcagacgga ttttcgactt acatgagaaa     360
ctgcataaaa aaaggagct ggctttttac caattcctcg attcattttc acaagaagaa      420
caaaaggctg tattgaagtt tctagagcag ttgacgtcaa cacttgaagc agaacaaacc     480
gatgggactc cagacaaacc tgtaaag                                         507

<210> SEQ ID NO 6
<211> LENGTH: 169
<212> TYPE: PRT
<213> ORGANISM: Bacillus subtilis

<400> SEQUENCE: 6

Met Ser Asp Leu Thr Lys Gln Met Ile Tyr Asp Ile Tyr Val Arg Leu
1               5                   10                  15

Leu His Leu Asn Glu Gln Lys Ala Asn Thr Ser Leu Gln Gln Phe Phe
            20                  25                  30

Lys Glu Ala Ala Glu Glu Asp Val Ala Glu Ile Pro Lys Asn Met Thr
        35                  40                  45

Ser Ile His Val Ile Asp Cys Ile Gly Gln His Glu Pro Ile Asn Asn
    50                  55                  60

Ala Gly Ile Ala Arg Lys Met Asn Leu Ser Lys Ala Asn Val Thr Lys
65                  70                  75                  80

Ile Ser Thr Lys Leu Ile Lys Glu Glu Phe Ile Asn Ser Tyr Gln Leu
                85                  90                  95

Thr Asp Asn Lys Lys Glu Val Tyr Phe Lys Leu Thr Arg Lys Gly Arg
            100                 105                 110

Arg Ile Phe Asp Leu His Glu Lys Leu His Lys Lys Lys Glu Leu Ala
        115                 120                 125

Phe Tyr Gln Phe Leu Asp Ser Phe Ser Gln Glu Glu Gln Lys Ala Val
    130                 135                 140

Leu Lys Phe Leu Glu Gln Leu Thr Ser Thr Leu Glu Ala Glu Gln Thr
145                 150                 155                 160

Asp Gly Thr Pro Asp Lys Pro Val Lys
                165

<210> SEQ ID NO 7
```

<211> LENGTH: 753
<212> TYPE: DNA
<213> ORGANISM: Bacillus subtilis

<400> SEQUENCE: 7

```
gtgaatgaga tgaccggaat ggtaacggaa agaaggtctg tgcattttat tgctgaggca      60
ttaacagaaa actgcagaga aatatttgaa cggcgcaggc atgttttggt ggggatcagc     120
ccatttaaca gcaggttttc agaggattat atttacagat taattggatg ggcgaaagct     180
caatttaaaa gcgtttcagt tttacttgca gggcatgagg cggctaatct tctagaagcg     240
cttggaactc cgagaggaaa ggctgaacga aagtaagga agaggtatc acgaaacagg       300
agatttgcag aaagagccct tgtggctcat ggcggggatc cgaaggcgat tcatacattt     360
tctgatttta tagataacaa agcctaccag ctgttgagac aagaagttga acatgcattt     420
tttgagcagc ctcatttcg acatgcttgt ttggacatgt ctcgtgaagc gataatcggg      480
cgtgcgcggg cgtcagttt gatgatgaa gaagtcagtg aggatatgct gaatttggct      540
gtggaatatg tcatagctga gctgccgttt tttatcggag ctccggatat tttagaggtg     600
gaagagacac tccttgctta tcatcgtccg tggaagctgg gtgagaagat cagtaaccat     660
gaattttcta tttgtatgcg gccgaatcaa gggtatctca ttgtacagga aatggcgcag     720
atgctttctg agaaacggat cacatctgaa gga                                   753
```

<210> SEQ ID NO 8
<211> LENGTH: 251
<212> TYPE: PRT
<213> ORGANISM: Bacillus subtilis

<400> SEQUENCE: 8

Met Asn Glu Met Thr Gly Met Val Thr Glu Arg Arg Ser Val His Phe
1               5                   10                  15

Ile Ala Glu Ala Leu Thr Glu Asn Cys Arg Glu Ile Phe Glu Arg Arg
            20                  25                  30

Arg His Val Leu Val Gly Ile Ser Pro Phe Asn Ser Arg Phe Ser Glu
        35                  40                  45

Asp Tyr Ile Tyr Arg Leu Ile Gly Trp Ala Lys Ala Gln Phe Lys Ser
    50                  55                  60

Val Ser Val Leu Leu Ala Gly His Glu Ala Ala Asn Leu Leu Glu Ala
65                  70                  75                  80

Leu Gly Thr Pro Arg Gly Lys Ala Glu Arg Lys Val Arg Lys Glu Val
                85                  90                  95

Ser Arg Asn Arg Arg Phe Ala Glu Arg Ala Leu Val Ala His Gly Gly
            100                 105                 110

Asp Pro Lys Ala Ile His Thr Phe Ser Asp Phe Ile Asp Asn Lys Ala
        115                 120                 125

Tyr Gln Leu Leu Arg Gln Glu Val Glu His Ala Phe Phe Glu Gln Pro
    130                 135                 140

His Phe Arg His Ala Cys Leu Asp Met Ser Arg Glu Ala Ile Ile Gly
145                 150                 155                 160

Arg Ala Arg Gly Val Ser Leu Met Met Glu Glu Val Ser Glu Asp Met
                165                 170                 175

Leu Asn Leu Ala Val Glu Tyr Val Ile Ala Glu Leu Pro Phe Phe Ile
            180                 185                 190

Gly Ala Pro Asp Ile Leu Glu Val Glu Glu Thr Leu Leu Ala Tyr His
        195                 200                 205

```
Arg Pro Trp Lys Leu Gly Glu Lys Ile Ser Asn His Glu Phe Ser Ile
    210                 215                 220
Cys Met Arg Pro Asn Gln Gly Tyr Leu Ile Val Gln Glu Met Ala Gln
225                 230                 235                 240
Met Leu Ser Glu Lys Arg Ile Thr Ser Glu Gly
                245                 250
```

<210> SEQ ID NO 9
<211> LENGTH: 18
<212> TYPE: DNA
<213> ORGANISM: Bacillus subtilis

<400> SEQUENCE: 9
catgggagag acctttgg                                                18

<210> SEQ ID NO 10
<211> LENGTH: 17
<212> TYPE: DNA
<213> ORGANISM: Bacillus subtilis

<400> SEQUENCE: 10
gtcggtcttc catttgc                                                 17

<210> SEQ ID NO 11
<211> LENGTH: 17
<212> TYPE: DNA
<213> ORGANISM: Bacillus subtilis

<400> SEQUENCE: 11
cgaccactgt atcttgg                                                 17

<210> SEQ ID NO 12
<211> LENGTH: 17
<212> TYPE: DNA
<213> ORGANISM: Bacillus subtilis

<400> SEQUENCE: 12
gagatgccaa acagtgc                                                 17

<210> SEQ ID NO 13
<211> LENGTH: 16
<212> TYPE: DNA
<213> ORGANISM: Bacillus subtilis

<400> SEQUENCE: 13
catgtccatc gtgacg                                                  16

<210> SEQ ID NO 14
<211> LENGTH: 17
<212> TYPE: DNA
<213> ORGANISM: Bacillus subtilis

<400> SEQUENCE: 14
caggagcatt tgatacg                                                 17

<210> SEQ ID NO 15
<211> LENGTH: 16
<212> TYPE: DNA
<213> ORGANISM: Bacillus subtilis

<400> SEQUENCE: 15
ccttcagatg tgatcc                                                  16

```
<210> SEQ ID NO 16
<211> LENGTH: 17
<212> TYPE: DNA
<213> ORGANISM: Bacillus subtilis

<400> SEQUENCE: 16
gtgttgacgt caactgc                                                    17

<210> SEQ ID NO 17
<211> LENGTH: 18
<212> TYPE: DNA
<213> ORGANISM: Bacillus subtilis

<400> SEQUENCE: 17
gttcagcctt tcctctcg                                                   18

<210> SEQ ID NO 18
<211> LENGTH: 18
<212> TYPE: DNA
<213> ORGANISM: Bacillus subtilis

<400> SEQUENCE: 18
gctaccttct ttcttagg                                                   18

<210> SEQ ID NO 19
<211> LENGTH: 18
<212> TYPE: DNA
<213> ORGANISM: Bacillus subtilis

<400> SEQUENCE: 19
cgtcaatatg atctgtgc                                                   18

<210> SEQ ID NO 20
<211> LENGTH: 17
<212> TYPE: DNA
<213> ORGANISM: Bacillus subtilis

<400> SEQUENCE: 20
ggaaagaagg tctgtgc                                                    17

<210> SEQ ID NO 21
<211> LENGTH: 17
<212> TYPE: DNA
<213> ORGANISM: Bacillus subtilis

<400> SEQUENCE: 21
cagctatcag ctgacag                                                    17

<210> SEQ ID NO 22
<211> LENGTH: 20
<212> TYPE: DNA
<213> ORGANISM: Bacillus subtilis

<400> SEQUENCE: 22
gctcagctat gacatattcc                                                 20

<210> SEQ ID NO 23
<211> LENGTH: 17
<212> TYPE: DNA
<213> ORGANISM: Bacillus subtilis

<400> SEQUENCE: 23
gatcgtcttg attaccg                                                    17
```

<210> SEQ ID NO 24
<211> LENGTH: 16
<212> TYPE: DNA
<213> ORGANISM: Bacillus subtilis

<400> SEQUENCE: 24
agctttatcg gtgacg                                              16

<210> SEQ ID NO 25
<211> LENGTH: 16
<212> TYPE: DNA
<213> ORGANISM: Bacillus subtilis

<400> SEQUENCE: 25
tgagcacgat tgcagg                                              16

<210> SEQ ID NO 26
<211> LENGTH: 17
<212> TYPE: DNA
<213> ORGANISM: Bacillus subtilis

<400> SEQUENCE: 26
cattgcggag acattgc                                             17

<210> SEQ ID NO 27
<211> LENGTH: 26
<212> TYPE: DNA
<213> ORGANISM: Bacillus subtilis

<400> SEQUENCE: 27
tagacaattg gaagagaaaa gagata                                   26

<210> SEQ ID NO 28
<211> LENGTH: 20
<212> TYPE: DNA
<213> ORGANISM: Bacillus subtilis

<400> SEQUENCE: 28
ccgtcgctat tgtaaccagt                                          20

<210> SEQ ID NO 29
<211> LENGTH: 18
<212> TYPE: DNA
<213> ORGANISM: Bacillus subtilis

<400> SEQUENCE: 29
catgggagag acctttgg                                            18

<210> SEQ ID NO 30
<211> LENGTH: 24
<212> TYPE: DNA
<213> ORGANISM: Bacillus licheniformis

<400> SEQUENCE: 30
gaattcgcag gaggaacgag tatg                                     24

<210> SEQ ID NO 31
<211> LENGTH: 24

```
<212> TYPE: DNA
<213> ORGANISM: Bacillus licheniformis

<400> SEQUENCE: 31
aagcttgaag atcagtgagg cagc                                              24
```